United States Patent [19]

Shuler et al.

[11] Patent Number: 5,429,640
[45] Date of Patent: Jul. 4, 1995

[54] INTRAMEDULLARY ROD FOR FRACTURE FIXATION OF FEMORAL SHAFT INDEPENDENT OF IPSILATERAL FEMORAL NECK FRACTURE FIXATION

[75] Inventors: Thomas E. Shuler, Pittsburgh, Pa.; Robert A. Latour, Jr., Clemson, S.C.

[73] Assignees: Clemson University, Clemson; Greenville Hospital System, Greenville, both of S.C.

[21] Appl. No.: 982,291

[22] Filed: Nov. 27, 1992

[51] Int. Cl.⁶ .............................................. A61F 5/04
[52] U.S. Cl. ..................................... 606/64; 606/62; 606/67
[58] Field of Search ..................... 606/62, 64, 63, 65, 606/67, 72, 73, 96, 98, 104; 623/16

[56] References Cited

U.S. PATENT DOCUMENTS

| | | |
|---|---|---|
| 1,951,278 | 3/1934 | Ericsson . |
| 2,518,019 | 8/1950 | Kane ..................... 606/62 |
| 2,531,734 | 11/1950 | Hopkins . |
| 2,761,444 | 9/1956 | Luck . |
| 4,055,172 | 10/1977 | Ender et al. . |
| 4,506,662 | 3/1985 | Anapliotis . |
| 4,622,959 | 11/1986 | Marcus . |
| 4,705,027 | 11/1987 | Klaue . |
| 4,817,591 | 4/1989 | Klaue . |
| 4,846,162 | 7/1989 | Meohring . |
| 4,865,025 | 8/1989 | Buzzi et al. . |
| 4,877,019 | 10/1989 | Vives . |
| 4,881,535 | 11/1989 | Sohngen . |
| 4,911,153 | 3/1990 | Border . |
| 4,913,137 | 4/1990 | Azer et al. . |
| 4,928,679 | 5/1990 | Chagneau et al. ........... 606/62 |
| 4,981,481 | 1/1991 | Kranz et al. ........... 606/62 |
| 4,988,350 | 1/1991 | Herzberg . |
| 5,009,664 | 4/1991 | Sievers ........... 623/16 |
| 5,032,125 | 7/1991 | Durham et al. ........... 606/62 |
| 5,053,035 | 10/1991 | McLaren ........... 606/67 |
| 5,057,103 | 10/1991 | Davis ........... 606/63 |
| 5,057,110 | 10/1991 | Kranz et al. ........... 606/62 |
| 5,084,053 | 1/1992 | Ender ........... 606/104 |
| 5,122,141 | 6/1992 | Simpson et al. ........... 606/62 |
| 5,122,146 | 6/1992 | Chapman et al. ........... 606/102 |
| 5,176,681 | 1/1993 | Lawes et al. ........... 606/64 |
| 5,201,735 | 4/1993 | Chapman et al. ........... 606/67 |

OTHER PUBLICATIONS

Harryman et al., "Ipsilateral Femoral Neck and Shaft Fractures. Report of Two Cases Using an Alternative Technique," pp. 183–188; 1986; *Clinical Orthopedics and Related Research*.

Browner et al., "Current Status of Locked Intramedullary Nailing: A Review," pp. 183–195; 1987; *Journal of Orthopaedic Trauma*, Raven Press Ltd., New York.

Klelmm et al., "Interlocking Nailing of Complex Fractures of the Femur and Tibia," pp. 89–100, Nov. 1986; No. 212, *Clinical Orthopedics & Related Research*, K. B. Lippincott Company, Philadelphia, Pa.

(List continued on next page.)

*Primary Examiner*—Peter A. Aschenbrenner
*Assistant Examiner*—Guy V. Tucker
*Attorney, Agent, or Firm*—Dority & Manning

[57] ABSTRACT

A femoral intramedullary rod has a thin or reduced proximal segment so as to provide room for the use of femoral hip screws. Use of the rod for femoral shaft fixation permits subsequent independent treatment of an ipsilateral femoral hip fracture as an isolated injury, regardless of whether initially detected. Different rod embodiments are formed by the omission of different proximal portions of the rod. It is in such portions that the femoral screws may be placed to set hip fractures. The rod is cannulated for installation over a guide wire. Internal rod threads, below the thin proximal segment in some embodiments, are used for initial installation of the rod with a driving member screwed into such threads. Without driving forces on the thin proximal segment, such segment can be made even thinner. Once the rod is seated, hip screws may be installed if there is a detected hip fracture. Subsequent to healing, the femoral screws and interlocking screws (if any) may be removed. A hollow reamer sized for clearance over the intramedullary rod may be placed down over the top of the rod to cut away any bony tissue ingrown into the proximal end. Thereafter, the rod is extracted with a suitable extraction device.

23 Claims, 17 Drawing Sheets

OTHER PUBLICATIONS

Skjeldal et al., "Interlocking Medullary Nails–Radiation Doses In Distal Targeting," pp. 179–181; 1987; vol. 106, *Archives of Orthopedic & Traumatic Surgery.*

Pennig et al., "A New Distal Aiming Device for Locking Nail Fixation," pp. 1725–1727; Dec. 1988; vol. 11, No. 12, *Operative Technique Section,* Klinik und Poliklinik, Munster, West Germany.

Hudson, "Locking nailing: an aid to distal targetting," pp. 129, 130; 1989; vol. 20, No. 3, Injury: *The British Journal of Accident Surgery,* London, Eng.

MacMillan et al., "A Simplified Technique of Distal Femoral Screw Insertion for the Gross–Kempf Interlocking Nail," pp. 252–259; Jan. 1988; No. 226, *Clinical Orthopedics and Related Research.*

Swiontkowski, "Ipsilateral Femoral Shaft & Hip Fractures," pp. 73–84; Jan. 1987; vol. 18, No. 1, *Orthopedic Clinics of North America.*

Gill et al., "Ipsilateral Fractures of the Femoral Neck & Shaft," pp. 293–298; 1990; vol. 4, No. 3, *Journal of Orthopaedic Trauma,* Raven Press, Ltd., N.Y.

Bucholz et al., "Concomitant Ipsilateral Fractures of the Hip & Femur Treated with Interlocking Nails," pp. 1402–1406; Nov. 1985; vol. 8, No. 11, *Orthopedics Magazine.*

Swiontkowski et al., "Ipsilateral Fractures of the Femoral Neck & Shaft," pp. 260–268; Feb. 1984; vol. 66–A, No. 2, *The Journal of Bone and Joint Surgery, Inc.*

Geissler et al., "Operative Management of Ipsilateral Fractures of the Hip & Femur," pp. 297–302; 1988; vol. 2, No. 4, *Journal of Orthopaedic Trauma,* Raven Press Ltd., New York.

"Femur: Trauma," pp. 513–520; 1990; *Orthopedic Knowledge Update Three, American Academy of Orthopedic Surgeons.* Author unknown.

Wiss et al., "Ipsilateral Fractures of the Femoral Neck & Shaft," pp. 159–166; 1992; vol. 6, No. 2, *Journal of Orthopaedic Trauma,* Raven Press Ltd., N.Y.

DeLee, "Fractures & Dislocations of the Hip," pp. 1211–1279; 1984; vol. 2, 2nd Ed., *Rockwood and Green: Fractures in Adults.*

Muller et al., "Femur Proximal," pp. 136, 137; 1991; 3rd Ed., *Springer–Verlag, Manual of Internal Fixation.*

Hughes et al., "The Role of Computerized Tomography in the Diagnosis of an Occult Femoral Neck Fracture Associated With an Ipsilateral Femorl Shaft Fracture:Case Report," pp. 296–298; Feb. 1991; vol. 31, No. 2, *The Journal of Trauma,* The Williams & Wilkins Company.

"Trauma: Femur," pp. 369–376; 1987; *Orthopedic Knowledge Update II, American Academy of Orthopedic Surgeons.* Author unknown.

"The Uniflex Nailing System, Surgical Technique," pp. cover–16; Undated; Biomet, Inc., Warsaw, Indiana, Form Y-BMT-114/013189. Author unknown.

Crouch, "Functional Human Anatomy, 2nd. Ed.," pp. cover & 158–161; 1972; Henry Kimpton Publishers, London (printed in U.S.A.).

"Gray's Anatomy," pp. cover & 183–191; 1974; Running Press Book Publishers, Philadelphia, Pennsylvania. Author unknown.

Jensen et al., "Engineering Drawing & Design, 3rd Ed.," pp. cover & 178, 179; 1985; McGraw–Hill Book Company, Gregg Division, New York.

Sheet of Three Figures concerning Uniflex Nailing System & article by Swiontkowski; 1 page; Unknown & 1987, respectively.

Intraflex Interim Intramedullary Pins; 5402–05 Intraflex Long Extracter with Hook & 5402–06 Intraflex Replacement Hook; 1 page "B 68"; Undated; Zimmer, Inc.

Instruments for Medullary Nails; 1 page No. 3–21; May 1987; Synthes, Inc.

Iniversal Nail Insertion Instrument Set; 1 page No. 1–89S; Jan. 1990; Synthes, Inc.

Harper et al., "Curvature of the Femur and the Proximal Entry Point for an Intramedullary Rod," pp. 155–161, 1987, *Clinical Orthopaedica and Related Research.*

Tencer et al., "Biomechanical Considerations in Intramedullary Nailing of Femoral Shaft Fractures," pp. 1–5, 1988, *Techniques in Orthopaedics.*

Johnson K. D., "Femoral Shaft Fractures," pp. 1560–1569, 1992, in *Skeletal Trauma,* vol. 2, W. B. Saunders, Philadelphia, Pa.

Johnson K. D., "Femoral Shaft Fractures," pp. 1598–1606, 1992, in *Skeletal Trauma,* vol. 2, W. B. Saunders, Philadelphia, Pa.

Bennett F. et al., "Treatment of Ipsilateral Fractures of the Hip and Formal Shaft," pp. 480–481, 1992, *Jorunal of Orthopaedic Trauma.*

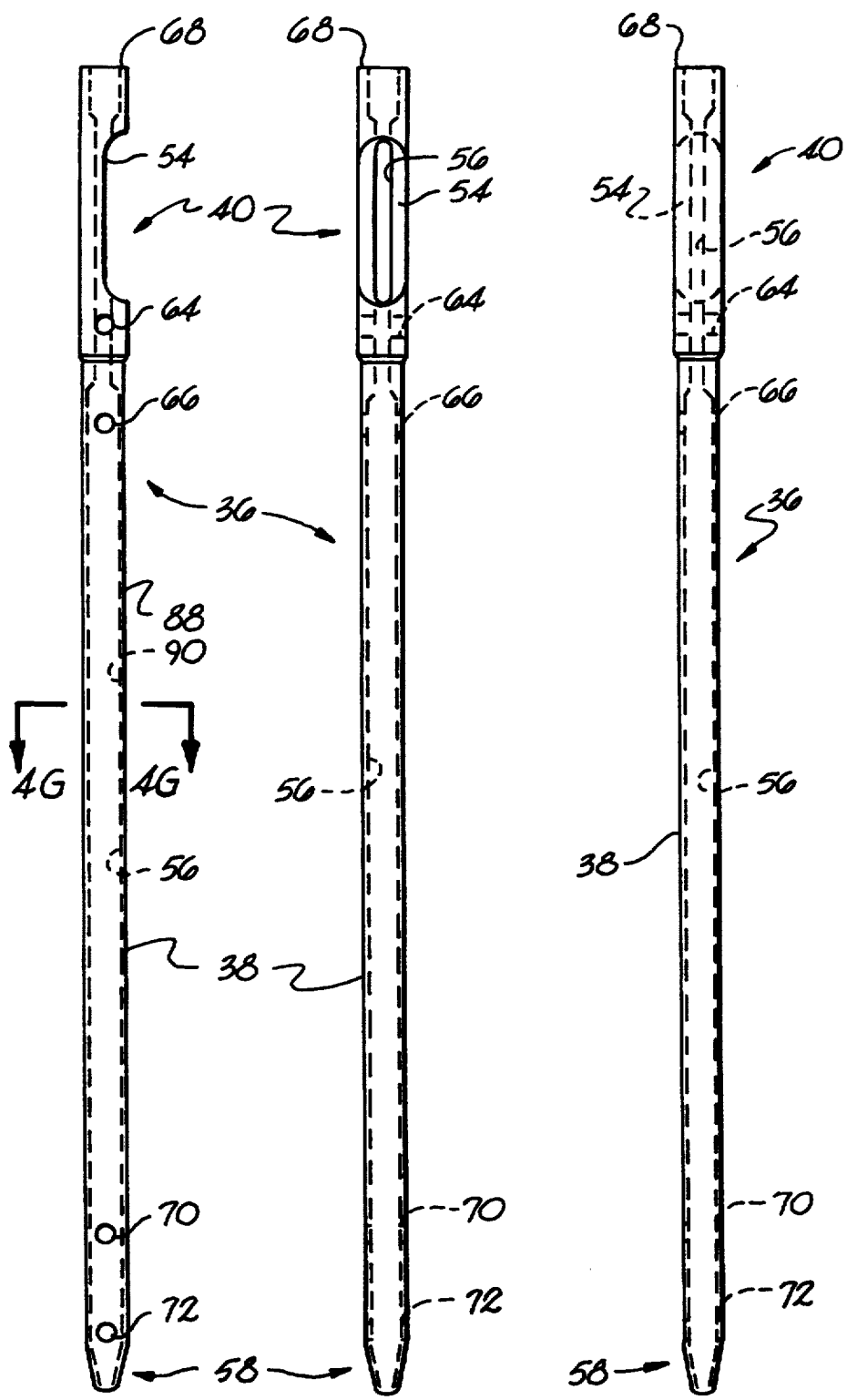

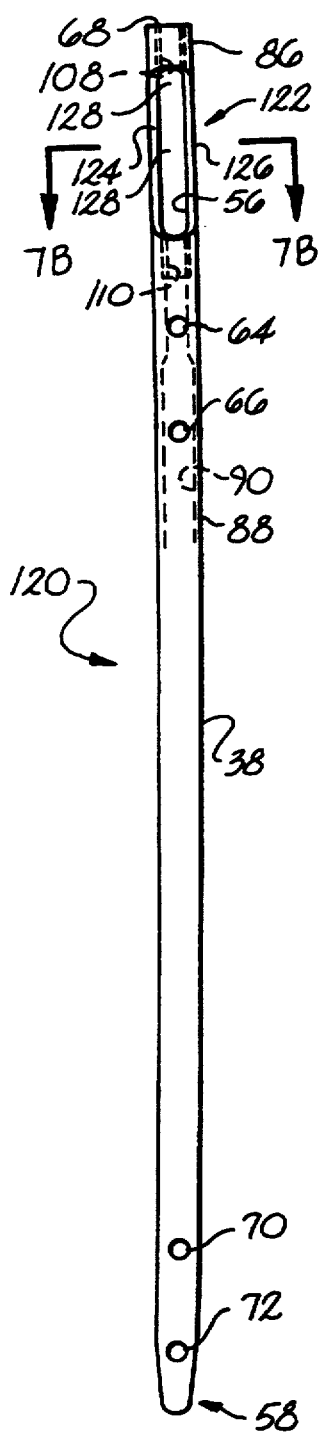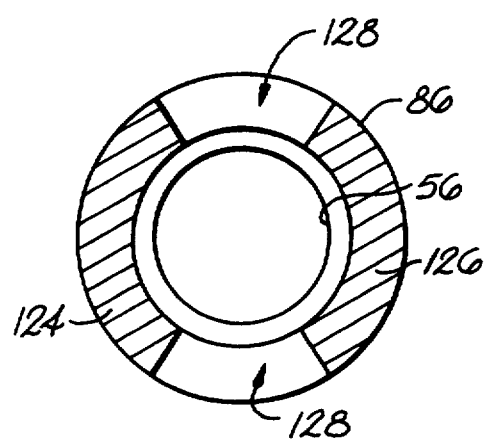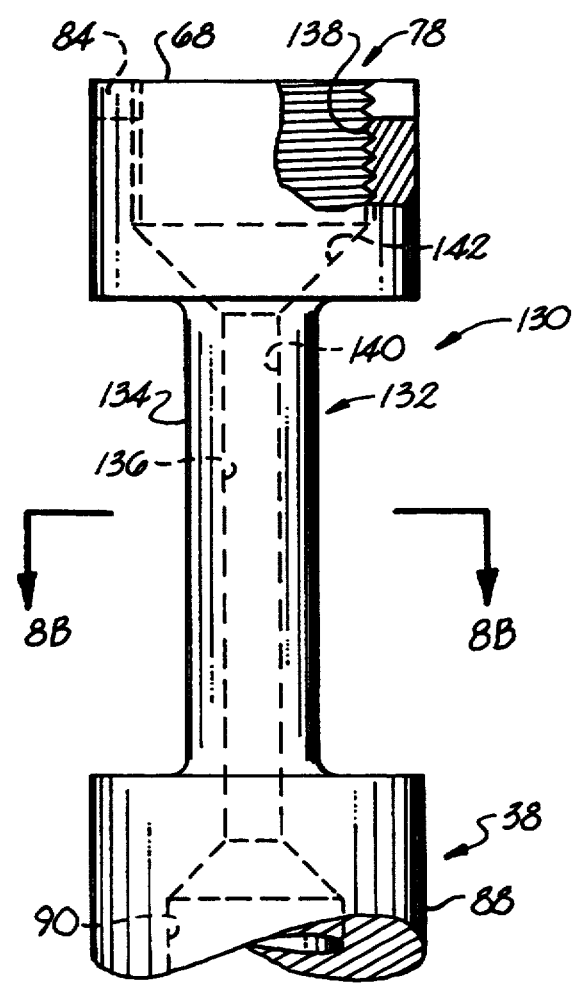
Fig. 7A
Fig. 7B
Fig. 8A

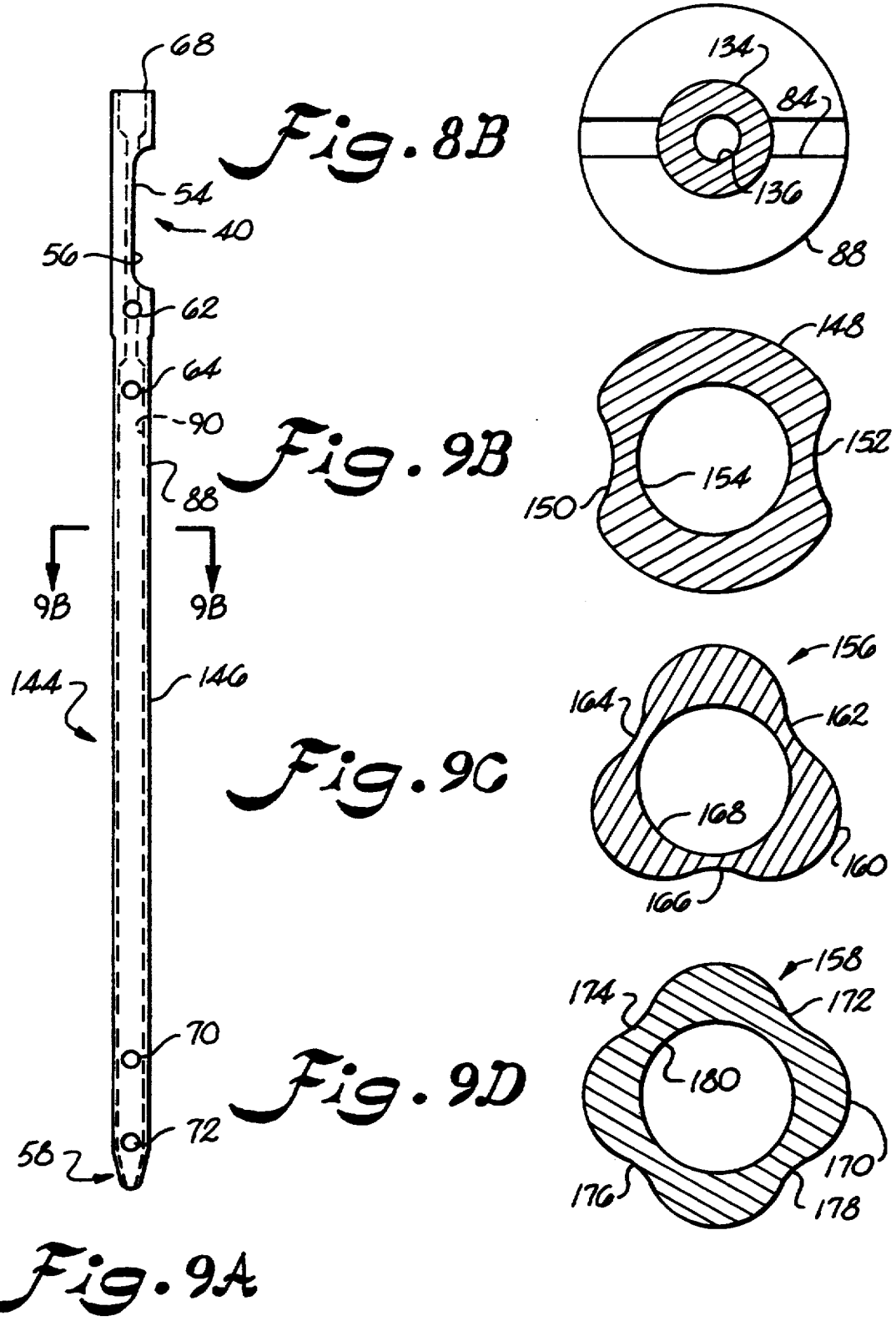

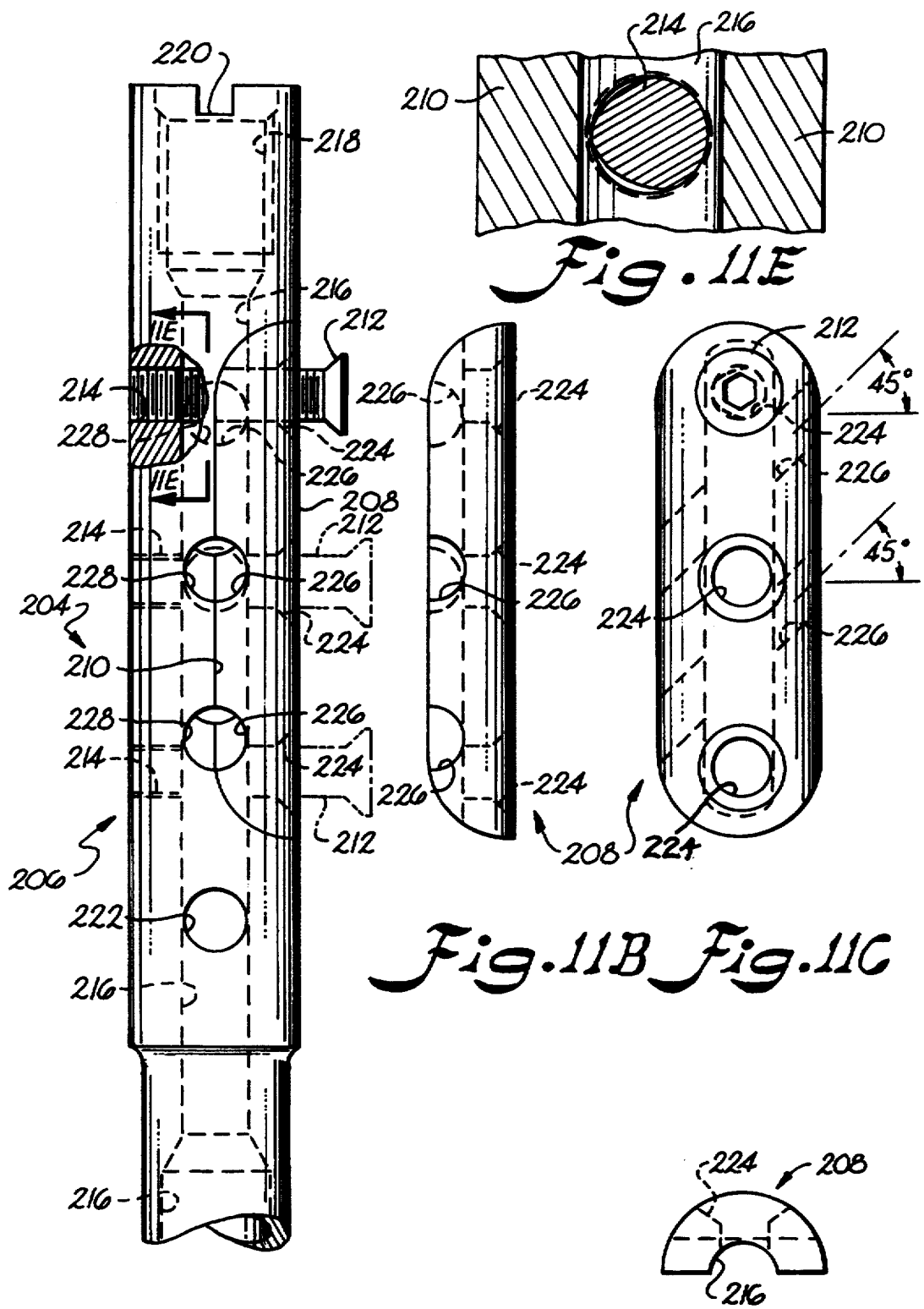

INTRAMEDULLARY ROD FOR FRACTURE FIXATION OF FEMORAL SHAFT INDEPENDENT OF IPSILATERAL FEMORAL NECK FRACTURE FIXATION

BACKGROUND OF THE INVENTION

The present invention relates in general to improved treatment for fractures of the femur and in particular concerns apparatus and methodology for the efficacious treatment of the highly problematic combination of a femoral shaft fracture with an ipsilateral femoral neck fracture (i.e., femoral hip region fracture).

The femur or thigh bone is the largest and longest bone in the human skeleton. In general, it comprises two extremities connected by an elongated fairly cylindrical shaft. The upper or proximal extremity may be broadly regarded as constituting the hip region.

Generally speaking, fracture injuries to the femoral shaft have been primarily treated (per current acceptable methods) with various intramedullary rods or nails. An intramedullary rod is an elongated member which is introduced to and resides in the marrow of the femur for the purpose of stabilizing the fractured femoral shaft. It is desired that stabilization take place in conjunction with anatomic reduction (i.e., proper reorientation of fractured elements to their original position, both relative to one another and relative to other adjacent anatomical features). As well known to those of ordinary skill in the art, installation of intramedullary rods often involves passage through the upper extremity or hip region, and in fact results in the proximal end of the rod occupying a significant portion of the hip portion of the femur.

It is possible to sustain fracture injuries not only to the femoral shaft, but also to one or both of the femoral extremities. Of particular present concern is the occurrence of a fracture to the upper extremity, particularly to the head or neck regions of the femur. The primary problem addressed by this invention occurs whenever a femoral neck fracture (or any femoral hip region fracture generally) occurs at the same time and in the same femur (ipsilateral fractures) as a femoral shaft fracture. A straightforward problem arises from the fact that the standard presently acceptable treatment for femoral neck fractures primarily involves the use of bone screws which are introduced (at various angles and locations) to the femoral hip region. Thus, there exists literally a physical interference between the standard intramedullary rod provided for treating a femoral shaft fracture and the standard bone screws provided for treating a femoral hip region injury. Less apparent but just as serious problems and complications also arise due to the practicalities of installation procedures accompanying the use of such two standard techniques.

Therefore, a major problem exists in instances of ipsilateral femoral shaft and hip fractures in that the standard acceptable treatments for respective femoral shaft and hip fractures are substantially mutually exclusive. At present, there is no standard accepted treatment method for ipsilateral femoral shaft and hip fractures, despite the availability of numerous different approaches. In some instances, the treating doctors even choose to forgo treatment of the shaft fracture until at least partial recuperation of the hip fracture, since highly precise fracture reduction is not as critical in the femoral shaft as it is in the hip. In other words, if the doctor thinks in a given situation that he cannot "fix" both problems in an ipsilateral fracture case, he or she may risk potential negative consequences of poor shaft fracture healing (e.g., limp or discomfort from shortened leg or misalignment) versus potential negative consequences of poor hip fracture healing (e.g., artificial hip replacement surgery).

The difficulties of the central problem may be better comprehended with a more detailed understanding of the anatomical considerations and of exemplary prior treatment approaches and drawbacks. The following very briefly outlines pertinent anatomical terminology with reference to present FIG. 1. FIG. 1 illustrates a generally anterior (front) surface view of a right human femur generally 20. Femur 20 is comprised of an inferior or distal extremity generally 22, a superior or proximal extremity generally 24, and an elongated generally cylindrical shaft 26 connecting the two opposing extremities. In the anterior view of present FIG. 1, the medial side of femur 20 is generally the right-hand illustrated side while the lateral side thereof is generally the left-hand illustrated side in the view.

The superior extremity generally 24 includes a number of separately recognizable features of present interest, including a head generally 28, a neck region generally 30, and greater and lesser trochanters generally 32 and 34, respectively. The greater trochanter is a relatively large and somewhat irregular eminence located above the top of the shaft and towards the lateral side of the neck, while the lesser trochanter constitutes a somewhat smaller (but of variable size in different patients) projection from the relatively lower and posterior (back) side of the femoral neck. Generally speaking, the "hip" may be regarded as comprising the features proximal to (i.e., above) the lesser trochanter 34.

Though not shown in detail in the illustration of present FIG. 1, a slight surface crest extends anteriorly and posteriorly between the trochanters 32 and 34. Also, an imaginary line or plane extending between the greater and lesser trochanters is referred to as the intertrochanteric line. Fractures can occur in may varieties in the hip. Generally speaking, fractures occurring between the intertrochanteric line and the head 28 are referred to as neck fractures. An intertrochanteric fracture is one generally in alignment with the intertrochanteric line, while a pertrochanteric fracture is one which resides at least in part in the neck region but which crosses the intertrochanteric line. A subtrochanteric fracture is still in the hip but at least partly below the intertrochanteric line.

Fracture patterns are the subject of much study and analysis. For example, one classification system referred to as Pauwels' classification grades femoral neck fractures into three types, depending on the angle the fracture forms with an imaginary horizontal plane resting across the extreme proximal end of the femur. Determination of such classification in a given instance (such as from x-rays or the like) helps the treating physician determine the desired positioning of femoral neck screws for treatment of the fracture. Generally speaking, greater strength is established whenever the screws normally address (i.e., are perpendicular to) the fracture line. Hence, the nature of the hip fracture can dictate the desired (or required) positioning of screws in the hip region, which indicated positions can be in conflict with the needed placement or effective space requirements of a standard intramedullary rod for treating an accompanying shaft fracture.

Also, a lateral view x-ray is virtually required to insure satisfactory anatomical reduction of a femoral neck fracture. However, many of the currently available shaft nail systems incorporate structures, such as a lateral fixation plate or similar, which literally would block the necessary x-ray view. See, for example, U.S. Pat. No. 4,506,662 issued to Anapliotis, and illustrating an exemplary attachment plate 40 in FIG. 4 thereof. FIG. 2b of such '662 patent also illustrates a technique referred to as "bundle" nailing, which can literally block out (or fill) an entire hip region to the exclusion of femoral screws needed for treatment of a femoral hip fracture.

Femoral shaft fractures are likewise the subject of much study and analysis, and can be variously classified. One accepted system is referred to as the Winquist-Hansen Comminution Scale, which focuses attention on the cortical damage to the femur. The femur is comprised of cortical bone, which is the dense rim of bone forming portions such as the annular portion of the shaft, and of marrow, which is the soft bone tissue received in the internal cavity defined by the cortical bone. On the Winquist-Hansen scale, a first type injury involves a fracture (i.e., break) to cortical bone in the shaft. The next higher level injury involves some loss (through absence, crushing, pulverizing, or other destructive effects) of the cortical bone, but less than fifty percent loss in a given region. The next higher type of fracture involves the same damage characteristics as above, but with greater than fifty percent cortical bone loss in a given region. The next higher type of injury involves trauma to such an extent that there is no remaining cortical bone contact in a given region. The highest type of injury on the communition scale involves actual segmental bone loss.

The importance in understanding the above-described progressive degrees of injury which can result from trauma to the femur arises from understanding the corresponding conventional treatments thereof. Generally speaking, the goal of any fracture treatment is to provide a stable and complete anatomic reduction (i.e., "setting") of the fracture.

As the nature of a fracture is progressively more severe, as described above, the treatment approaches become more complex and more difficult to administer. For example, one of the more simple approaches to treatment of femoral shaft injuries involves the use of relatively smaller diameter, or in some instances, even flexible, intramedullary rods. A smaller diameter rod is typically less strong but may avoid the need to literally ream (i.e., cut) out a channel inside the femur for insertion of the rod. Sometimes, an anatomic reduction of adequate mechanical stability can be achieved through the introduction of a guide wire or similar in the top of the shaft and down through the bone marrow, followed by introduction of a cannulated (i.e., hollow) femoral nail or rod over the top of the guide wire. However, an inadequate biomechanically stable fixation pattern can result in various complications, such as non-union or malunion, or even shortening and malrotation. In worst case complications, there can be osteonecrosis (tissue death). Even in younger patients, such events can lead to the need for hip replacement surgery (highly undesirable for any patient, but regarded especially as potentially devastating to younger patients).

To satisfy reduction and stability needs, femoral shaft injuries, particularly those of greater severity, often entail treatment with larger diameter or more stiff femoral nails, which can involve reaming techniques for placement of the nail. Such techniques literally involve reaming out part of the femur interior to be followed by installation of the nail. In many instances, so-called second generation or reconstruction nails ("recon" nails) are utilized, which typically involves interlocking steps of inserting screws through the leg and femur into holes in the nail to secure the position of both the femur and the nail. Special targeting devices, assistants, and experience can be required for blindly seating interlocking screws inside of a femur.

In some patients, the use of intramedullary nails in an unreamed femur may be adequate for the treatment of inherently stable fractures, but the use of intramedullary nails in a reamed femur and/or the use of interlocking femoral nails are standard treatments for more severe injuries. A readily apparent drawback of such technique, however, relates to the installation process, being both costly in terms of the required special instruments, and for the personnel who must have special surgical training, and additional assistants. Since worser or worst case traumas typically occur less frequently, doctors tend to have (and can expect to have) generally less experience with the more severe situations. Such fact only compounds the difficulty of, for example, night time emergency room treatment of ipsilateral femoral fractures.

It has been reported that as many as 2.5 percent to 5 percent of femoral shaft fractures occur in combination with (i.e., ipsilaterally) with femoral hip fractures. Moreover, such combination fractures most often occur as a result of high energy trauma. The above description of standard treatments of more progressive fracture types (i.e., most likely occurring due to relatively higher energy trauma) provides a background for understanding the considerable difficulty of treating ipsilateral fractures. High energy trauma to the thigh region can occur in a variety of ways, such as due to high speed motorcycle accidents, car accidents, or falls from a relative height.

One exemplary analysis of high energy trauma leading to ipsilateral femoral fractures is as follows. The energy or force from a given traumatic impact must be dissipated somewhere or somehow. Very frequently, such dissipation takes the form of a fracture (i.e., break) in the femoral shaft, typically medial or distal thereto. If excess energy exists after partial dissipation through a femoral shaft fracture, then further energy dissipation must take place.

The femur or thigh is in an adducted position whenever the legs are close together and generally aligned with the trunk of the body. The femoral head resides in and articulates in the acetabulum. Whenever the femur is in such adducted position, excess energy dissipation often results in the hip being dislocated by escaping from the acetabulum. However, if the femur is in an abducted position (i.e., with the leg turned out or open, such as a rider on a motorcycle), the hip region of the femur cannot escape from the acetabulum and therefore must absorb the excess energy to be dissipated. Such events can result in one of the various hip fractures as described above, such as a neck fracture, intertrochanteric fracture, or other.

Other traumatic events can cause ipsilateral fractures "in reverse," (i e with the femoral hip fracturing before the femoral shaft. Resulting treatment complications are roughly the same, regardless of the originating trauma.

A generally accepted treatment for stabilizing femoral neck fractures is the use of multiple lag screws, such as in a triangular or some other deliberate pattern designed to gain needed fixation stability. However, reports indicate that as many as one third of the femoral neck fractures may be missed from an initial diagnosis. This means that a standard intramedullary nail may have already been used to fix a femoral shaft fracture, and therefore occupies the space in the hip within which the multiple lag screws should be inserted. Such an occurrence results in attempted placement around the prepositioned nail, but such approach can lead to inadequate mechanical stability for the femoral neck fracture. If, for example, Ender nails are utilized (nails which are placed upwardly through the distal end of the femur; see, for example, U.S. Pat. No. 4,055,172 issued to Ender et al.), there may be an inadequate and unstable anatomic reduction of the femoral shaft fracture. Therefore, no satisfactory standard treatment exists for treatment of the ipsilateral shaft and hip fractures as described above.

Traumatic injury of sufficiently high energy to cause ipsilateral femoral shaft and hip injuries may well result in multiple injuries or compound trauma to the patient. Significantly, pertinent literature analyzing and advocating various treatments of trauma patients has revealed handling of femoral fractures (i.e., stabilization thereof) to be an integral part of the overall resuscitation of such a trauma victim. Early stabilization of femoral fracture conditions has been shown to decrease the incidences of acute respiratory distress syndrome and death. Hence, there is potentially a great deal at stake whenever treatment standards have heretofore been generally unable to address particular fracture patterns (i.e.., ipsilateral femoral shaft and hip fractures) occurring most typically in trauma victims of the type most likely to also have other trauma related complications (i.e., multiple or compound injuries). Given such facts, it should be all the more apparent that treatments which involve time consuming, complex, or unfamiliar skill specific procedures are all the more contraindicated.

The patent literature describes different attempts at treating various femoral fractures, and thus provides additional background in this area. Further examples of such patents are:

| U.S. Pat. No. | INVENTOR | ISSUE DATE |
| --- | --- | --- |
| 2,761,444 | Luck | September 4, 1956 |
| 4,705,027 | Klaue | November 10, 1987 |
| 4,817,591 | Klaue | April 4, 1989 |
| 4,846,162 | Meohring | July 11, 1989 |
| 4,865,025 | Buzzi et al. | September 12, 1989 |
| 4,877,019 | Vives | October 31, 1989 |
| 4,988,350 | Herzberg | January 29, 1991 |

The disclosures of all the above-listed and above-referenced U.S. Patents are fully incorporated herein by reference.

SUMMARY OF THE INVENTION

The present invention recognizes and addresses various of the foregoing drawbacks and shortcomings, and others, concerning treatment of femoral fractures, particularly ipsilateral femoral shaft and hip fractures. Thus, broadly speaking, a principal object of this invention is improved treatment of ipsilateral femoral hip and shaft fractures. More particularly, a main concern is providing an efficacious treatment for such ipsilateral femoral fractures, adequate to provide a standard method of treatment for such difficult fracture patterns, which technology is presently generally lacking.

It is another more particular object of the present invention to provide a standard method of treatment for ipsilateral fracture patterns which is not overly technically demanding on the treating physician, thereby improving the quality of practice and broadening the availability of the treatment.

Still a further more particular object is to provide methodology and apparatus for a successful and an acceptable treatment approach for the above-described ipsilateral fracture patterns. More specifically, an object is to provide for adequate biomechanically stable hip and shaft fracture fixation, even whenever accompanied by significant femoral shaft comminution.

It is another more general object of the subject invention to provide an apparatus in the form of a new intramedullary rod design which results in adequate apparatus and corresponding methodology for the treatment of ipsilateral femoral hip and shaft fractures while addressing the foregoing various concerns and others of inadequate or inferior performance of currently available fracture treatments and techniques. More specifically, it is desired to provide a femoral intramedullary rod which has a specialized proximal segment of unique design such that, when installed in the femur, adequate space is still afforded for the use and presence of multiple bone screws. Such advantageous approach in accordance with practice of the subject invention, treatment of a femoral hip or neck fracture is rendered completely independent from the treatment of a shaft fracture, resulting in an idealized treatment approach for the physician.

Further, it is an object to make use of a new intramedullary rod design in accordance with this invention having such capabilities as to permit a treating physician or surgeon to utilize or rely on otherwise familiar techniques (generally speaking) for installation of such rod for femoral shaft fixation, while subsequently independently treating the femoral neck fracture by the use of multiple hip screws as if it were an isolated or separate injury. With such apparatus and through such treatment methodology, it is an object to permit later treatment of any femoral neck or otherwise hip located fracture which may be missed or otherwise omitted during initial assessment.

It is another present object to provide an improved intramedullary rod having a variously notched proximal segment to receive hip screws in such notched portions thereof for improved biomechanically stable fixation patterns for a femoral hip fracture while the seated rod addresses an existing ipsilateral femoral shaft fracture. It is a more particular object to provide such improved rod in specific embodiments for use with interlocking screws and without.

Still further objects of the present invention relate to providing accompanying installation and subsequent withdrawal apparatus and methodology for use with an intramedullary rod of the new design disclosed herewith.

Additional objects and advantages of the invention are set forth in, or will be apparent to those of ordinary skill in the art from, the detailed description which follows. Also, it should be further appreciated that modifications and variations to the specifically illustrated and discussed features, materials, and steps hereof may be practiced in various embodiments and uses of this invention without departing from the spirit and scope thereof, by virtue of present reference thereto. Such variations may include, but are not limited to, substitution of equivalent means and features, materials, or steps for those shown or discussed, and the functional or positional reversal of various parts, features, steps, or the like.

Still further, it is to be understood that different embodiments, as well as different presently preferred embodiments, of this invention may include various combinations or configurations of presently disclosed features, elements, steps, or their equivalents (including combinations of features or steps or configurations thereof not expressly shown in the figures or stated in the detailed description). One exemplary such embodiment of the present invention relates to a femoral intramedullary rod for the biomechanically stable anatomic reduction of a femoral shaft fracture while facilitating the independent treatment of an ipsilateral femoral hip fracture.

Such foregoing intramedullary rod preferably comprises an elongated cannulated shaft and a relatively short proximal cannulated shaft segment. More specifically, the shaft has a tip end for being seated in a femoral shaft with the tip end introduced in a relatively distal direction through the proximal extremity of a receiving fractured femur. The shaft segment is associated in axial alignment with the elongated rod shaft proximal thereto and opposite to the shaft tip end, for residing generally in a femoral hip region whenever the rod shaft is situated in a receiving femoral shaft. Such proximal shaft segment further preferably includes connection means for selectively interconnecting with drive components and extraction components for alternate installation and withdrawal, respectively, of the rod relative to a receiving femur, and the proximal shaft segment still further includes a relatively reduced cross-sectional area region forming a femoral hip screw passageway therethrough, so that femoral hip screws may be independently introduced into a femoral hip region for the treatment of fractures therein.

Another present exemplary embodiment concerns an intramedullary rod for the treatment of ipsilateral femoral hip and shaft fractures, comprising an elongated shaft with a relatively thin proximal segment for receipt of such segment in a femoral hip region with the shaft distal thereto so that space is provided for the independent introduction of at least one femoral hip screw relatively adjacent such segment.

Yet another construction comprising a present exemplary embodiment includes a treatment system for ipsilateral fracture patterns of the femoral hip and shaft, such system including a cannulated femoral intramedullary rod, driving means, a plurality of interlocking screws, interlocking screw guide means, and at least one femoral hip screw. In the foregoing exemplary system embodiment, the intramedullary rod preferably has a tapered distal end, an intermediate elongated shaft, a reduced cross-sectional area proximal end defining a passageway therethrough for femoral hip screws, at least one relatively distal interlocking screw hole, at least one relatively proximal interlocking screw hole, internal diameter proximal end connection thread means for the attachment of further components thereto, and registration means formed in such proximal end for guiding the positioning of further components relative to said rod;

The foregoing exemplary driving means may be removably operatively associated with the rod proximal end connection thread means, for selectively driving the intramedullary rod to a desired predetermined depth into a receiving fractured femur, with the rod proximal end received in the femoral hip region with the rod shaft distal thereto.

The plurality of interlocking screws are for receipt thereof in the interlocking screw holes. The interlocking screw guide means may be removably operatively associated with the rod proximal end connection thread means and the rod proximal end registration means, for aligning at least one of such interlocking screws for seating thereof in the at least one relatively proximal interlocking screw hole. The at least one femoral hip screw is provided for selected seating thereof through the rod proximal end passageway into the hip region of the receiving femur for stable anatomic reduction of a femoral hip fracture therein.

Various present embodiments also relate to corresponding treatment methods involving the present apparatuses. One exemplary such method relates to a method of treatment for ipsilateral femoral hip and shaft fractures, comprising providing an intramedullary rod having an elongated shaft with a relatively thin proximal segment; and seating such intramedullary rod in a fractured femur with the elongated shaft situated in the femoral shaft for treatment of a fracture therein, and with the relatively thin proximal segment situated in the femoral hip region. With such arrangement, space is provided for the subsequent independent introduction of at least one femoral hip screw relatively adjacent the rod proximal segment.

A further exemplary method of the invention is as set forth in the foregoing method, and further including the step of independently introducing at least one femoral hip screw relatively adjacent the rod proximal segment for treatment of a fracture in the femoral hip region.

Another exemplary present method concerns a treatment method for ipsilateral fracture patterns of the femoral hip and shaft, such method including the steps of providing a cannulated femoral intramedullary rod, having a tapered distal end, an intermediate elongated shaft, a reduced cross-sectional area proximal end defining a passageway therethrough for femoral hip screws, at least one relatively distal interlocking screw hole, at least one relatively proximal interlocking screw hole, internal diameter proximal end connection thread means for the attachment of further components thereto, and registration means formed in the proximal end for guiding the positioning of further components relative to such rod; providing rod driving means and removably operatively associating such driving means with the rod proximal end connection thread means; using the driving means for selectively driving the intramedullary rod to a desired predetermined depth into a receiving fractured femur, with such rod proximal end received in the femoral hip region with the rod shaft distal thereto for stable anatomic reduction of a femoral shaft fracture in the receiving femur; providing a plurality of interlocking screws for receipt thereof in the interlocking screw holes; providing interlocking screw guide means and removably operatively associating such guide means with the rod proximal end connection thread means and the rod proximal end registration means; using the guide means for aligning at least one of the interlocking screws for seating thereof in said at least one relatively proximal interlocking screw hole, and seating such screw in such proximal screw hole to further stabilize a femoral shaft fracture of the receiving femur; and providing at least one femoral hip screw and selectively seating such hip screw through the rod proximal end passageway into the hip region of the receiving femur for stable anatomic reduction of a femoral hip fracture therein.

Still further present embodiments concern additional improved devices for supporting use of present femoral intramedullary rods (as well as other forms of intramedullary rods). One such exemplary embodiment concerns an interlocking screw hole targeting apparatus for use with a femoral intramedullary rod of the type having a central longitudinal axis, proximal end connection means for securement of a further device thereto, proximal end registration means for alignment of a further device relative thereto, and at least one relatively proximal interlocking screw hole situated at a predetermined distance distal to the registration means, such targeting apparatus comprising rotational position control arm means, securement means, selectively operable clamping means, and targeting arm means.

The foregoing control arm means may be removably operatively associated with the rod proximal end registration means and operative for extending generally laterally therefrom in rotational alignment with the rod relatively proximal interlocking screw hole. The securement means are for removably securing such control arm means to the proximal end connection means of the intramedullary rod.

The foregoing exemplary selectively operable clamping means are movably supported on the lateral extension of the rotational position control arm means, for selectively clamping thereon at a selected distance radially outward from the central longitudinal axis of the intramedullary rod. The targeting arm means are secured to such clamping means for movement therewith and extending therebelow for parallel alignment thereby with the central longitudinal axis of the intramedullary rod, such targeting arm means having at least one interlocking screw target hole located a predetermined distance distal to the clamping means such as to align with the intramedullary rod screw hole. With practice of the foregoing arrangement, the intramedullary rod screw hole may be targeted for drilling through the femur and securing an interlocking screw in such intramedullary rod screw hole.

Those of ordinary skill in the art will better appreciate the features and aspects of such embodiments, methods, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended figures, in which:

FIGS. 4A, 4B, and 4C illustrate respectively a side view (looking in the medial direction), an anterior view, and a posterior view of a first embodiment of an exemplary intramedullary rod in accordance with the subject invention;

FIG. 7A illustrates a side view (in the medial direction) of a fourth exemplary embodiment of an intramedullary rod in accordance with the subject invention;

FIG. 7B illustrates a cross-sectional view in the proximal region of the exemplary embodiment of present FIG. 7A, taken along the sectional line 7B—7B indicated therein;

FIG. 8A illustrates (in enlargement) a side view of a proximal end portion of a fifth exemplary embodiment of an intramedullary rod in accordance with the subject invention;

FIG. 8B illustrates a cross-sectional view in the proximal region of the exemplary embodiment of present FIG. 8A, taken along the sectional line 8B—8B indicated therein;

FIG. 9A illustrates a side view (in the medial direction) of a general illustration of an exemplary intramedullary rod in accordance with the subject invention, representative of present optionally used variations in the shaft cross-section thereof;

FIG. 9B illustrates a cross-sectional view of the shaft of the exemplary embodiment of present FIG. 9A, taken along the sectional line 9B—9B indicated therein;

FIGS. 9C and 9D illustrate respective alternative cross-sectional rod shaft embodiments which may be practiced in place of the exemplary embodiment of present FIG. 9B, and which may be utilized in combination with other present exemplary proximal end portions and other features of the exemplary intramedullary rods disclosed herewith;

FIG. 11A illustrates (in enlargement of the proximal portion) a side view (in the medial direction) of a seventh exemplary embodiment of an intramedullary rod in accordance with the subject invention, particularly having modular components, with the selected addition of which converts the intramedullary rod from one type proximal end to another type thereof;

FIGS. 11B, 11C, and 11D illustrate respectively a side view (in the medial direction), an anterior view, and a bottom view of a modular component of the present exemplary embodiment of FIG. 11A;

FIG. 11E illustrates a cross-sectional view of an exemplary locking bolt such as used in the exemplary embodiment of present FIG. 11A, taken along the sectional line 11E—11E indicated therein;

Figure 1:
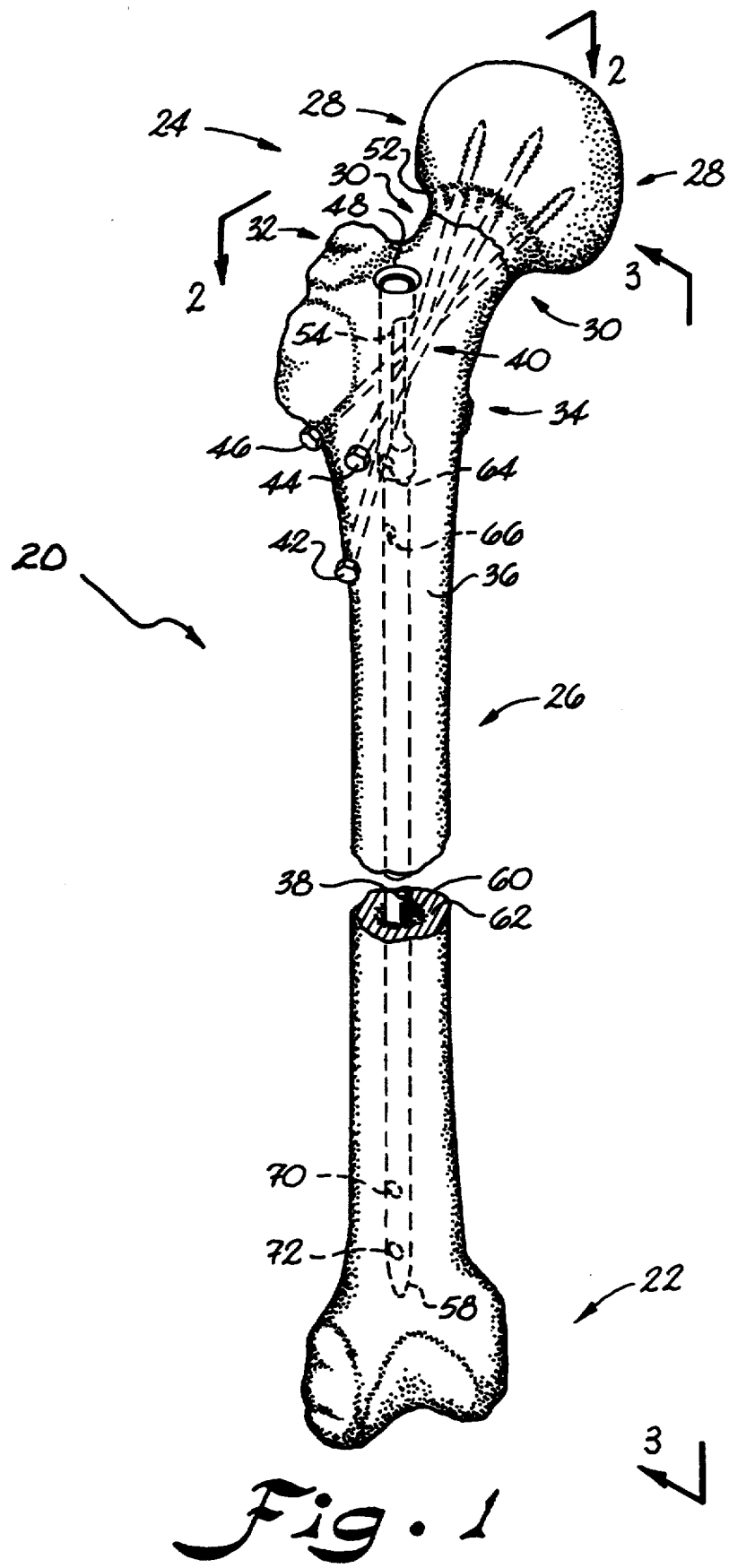
FIG. 1 is a generally anterior (frontal) somewhat isometric view of a right femur of the human skeleton, with an exemplary first embodiment of an intramedullary rod in accordance with the subject invention illustrated in dotted line therein, further in conjunction with a dotted line illustration of exemplary femoral hip screws.

Repeat use of reference characters throughout the present specification and appended drawings is intended to represent same or analogous features, elements, or steps of the invention.

DETAILED DESCRIPTION OF THE PREFERRED EMBODIMENTS

The following description sets forth numerous details both as to structural embodiments in accordance with the subject invention and present methodology. However, those of ordinary skill in the art will appreciate various broader aspects to the subject invention, taken from the following detailed description thereof, and which aspects are not expressly limited to the precise embodiments illustrated herewith or discussed herein. The present invention is intended to encompass all such variations, modifications, and the like as would be understood by those of ordinary skill in the art from the following.

Figure 2:
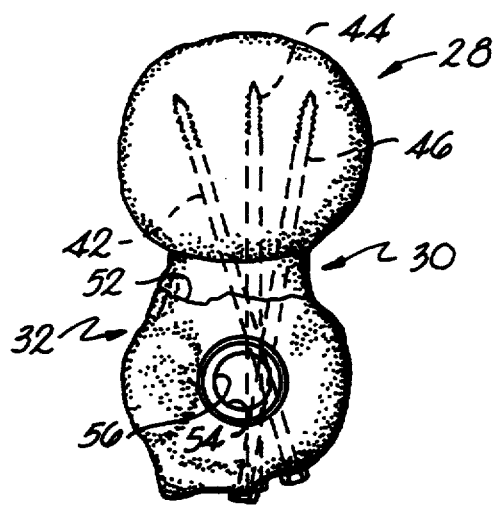
FIG. 2 is a top view of the FIG. 1 illustration, as seen from the view line 2—2 indicated therein.
Figure 3:
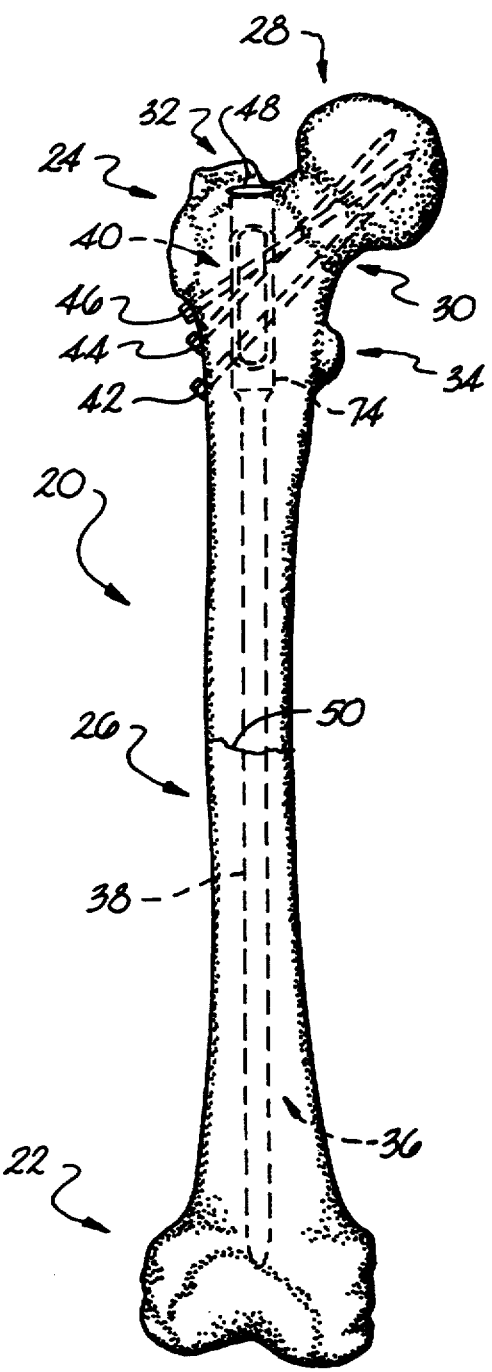
FIG. 3 is a fully anterior (front elevational) view of the FIG. 1 illustration, as seen from the view line 3—3 indicated therein.

Broadly speaking, present FIGS. 1–4 (including FIGS. 4A–4G) illustrate a first exemplary embodiment of an intramedullary rod in accordance with the subject invention. More specifically, FIGS. 1-3 illustrate one preferred installation of such rod in the femur generally 20 of a given patient. The anatomy of femur 20 is discussed in some detail in the Background portion of this specification, and familiarity with such discussion will be hereafter presumed.

FIG. 1 is a generally anterior somewhat isometric view of a right femur 20 of the human skeleton, with an exemplary first embodiment of an intramedullary rod generally 36 in accordance with the subject invention illustrated in dotted line therein (FIGS. 1 and 3). FIG. 2 is a top view of the FIG. 1 illustration, as seen from the view line 2—2 indicated therein. FIG. 3 is a fully anterior view of the illustration of FIG. 1, as seen from the view line 3—3 indicated therein.

FIGS. 4A, 4B, and 4C, illustrate respectively a side view (looking in the medial direction of the human skeleton right femur), an anterior view, and a posterior view of the first embodiment generally 36 of an exemplary intramedullary rod in accordance with the subject invention. As shown, rod 36 primarily comprises an elongated shaft 38 having a relatively thin proximal segment generally 40, which segment 40 is situated so as to be received in a femoral hip region with the shaft 38 distal thereto. As a result, space is provided in the femoral hip region for the independent introduction of femoral hip screws, such as exemplary screws 42, 44, and 46. Such hip screws are well known to those of ordinary skill in the art, without additional detailed description. In addition, particular details of such screws form no particular aspects of the subject invention, other than their useful combination with present embodiments of intramedullary rods and present methodology incorporating same and such femoral hip screws. Also, implantation rods, screws, and the like are typically formed of stainless steel or similar, all of which is well known to those of ordinary skill without further discussion.

FIGS. 1 through 3 very clearly illustrate the considerable advantage of the present invention, which is to permit the independent use of femoral hip screws for treatment of an ipsilateral femoral hip (or neck) fracture in combination with use of an intramedullary rod for treatment of a femoral shaft fracture. FIGS. 1 and 3 illustrate in dotted line and in partial cutaway (FIG. 1) the placement of rod 36 into femur 20 via an enlarged opening such as 48 formed in the proximal end 24 of such femur. For the sake of clarity, exemplary fracture patterns are primarily discussed in the Background of the subject specification, rather than illustrated throughout the figures. However, representative fracture line 50 of present FIG. 3 illustrates a femoral shaft fracture in an approximately medial shaft position, while representative fracture line 52 (FIGS. 1 and 2) illustrates an exemplary femoral hip region fracture. More specifically, hip fracture 52 is generally transverse across the neck region 30.

FIGS. 1 through 3 provide a very clear illustration of utilizating present exemplary femoral intramedullary rod 36 for the biomechanically stable anatomic reduction of the femoral shaft fracture 50 while facilitating the independent treatment of the ipsilateral femoral hip fracture 52 (through the use of hip screws 42, 44, and 46). Various hip screw patterns may be practiced in accordance with the subject invention. The representative triangular pattern of three screws at different placements and angles is one example of a particularly strong and stable arrangement. Other known arrangements of multiple lag screws or the like may be practiced in conjunction with the subject invention.

FIG. 2 in particular illustrates the femoral hip screw passageway advantageously provided in the proximal shaft segment generally 40 by the use of a relatively reduced cross-sectional area region 54. As best seen in FIGS. 1, 5a, and 5b in a preferred embodiment the passageway is defined through at least a 180 degrees of the circumference of the proximal shaft segment at least up to the longitudinal centerline of the shaft segment and elongated in the longitudinal direction which allows for independent and variable positioning of the hip screws through an angular range defined by the elongated passageway. In the illustrated example of present FIGS. 1 through 4, such region is situated in a relatively posterior position relative to the receiving femur 20, which means that the femoral hip screw passageway established thereby resides in a generally anterior position relative to such femur. Further embodiments of the subject invention as discussed disclose the structural arrangements for accommodating still further femoral hip screw placements.

As discussed in the Background of the specification, the location and nature of the hip fracture to be treated can substantially dictate the desired location or placement for hip pins, as well as the number of hip pins or screws to be used. The anterior position of the hip pins illustrated in present FIGS. 1 through 3 is one very typical (i.e., frequently encountered) placement. However, such placement would completely interfere with a conventional intramedullary rod having a substantially larger or solid proximal region with no femoral hip screw passageway formed therethrough. The passageway established through practice of the subject invention is entirely different from interlocking screw holes as utilized in some reconstructive type intramedullary rods, which holes have a preset location and angle (such as towards the hip), and which rods have the difficulty of targeting and penetrating the holes with the hip screws, while also properly seating the screws in relation to the hip fracture.

Present FIGS. 1 through 4 illustrate additional exemplary aspects of the subject invention aside from the femoral hip screw passageway provided thereby. For example, the full length of rod 36 may be cannulated (i.e., hollow), so as to define an inside diameter 56 along its length. With such arrangement, intramedullary rod 36 is useful with a guide wire, well known to those of ordinary skill in the art for establishing an initial pathway for either insertion of an intramedullary rod or a reaming device to further prepare for insertion of a rod. Reaming techniques are likewise known to those of ordinary skill in the art, without discussion of additional details herewith.

Another feature which may be practiced is the use of a tapered tip end generally 58 by which rod 36 is further aided in penetration of the medullary canal generally 60 of femur 20. The use of larger or stiffer nails, particularly when involving reaming operations, can include some degree of reaming of cortical bone 62 (the generally harder or dense rim of bone annularly along the length of femur shaft 26).

FIGS. 1 through 4 further illustrate optional use of interlocking screw holes, by which an intramedullary rod may further anatomically reduce and/or stabilize a fractured femur. While different numbers and placements of such interlocking screw holes may be practiced in various embodiments, the present exemplary embodiment 36 illustrates a pair of relatively proximal interlocking screw holes 64 and 66 located respective predetermined distal distances from proximal end 68 of rod 36. Devices in accordance with the subject invention for targeting such relatively proximal interlocking screw holes 64 and 66 are discussed in greater detail below, such as with reference to present FIGS. 13 through 15.

Similarly, relatively distal interlocking screw holes represented by holes 70 and 72 may be provided, likewise at known or predetermined distal distances from proximal end 68 of rod 36. Present FIG. 3 also represents practice of the present invention without use of interlocking screw holes.

FIGS. 1 through 4 represent another feature which may be optionally practiced, which is that the proximal region generally 40 of rod 36 may have a relatively larger outside diameter than the remainder of the rod, particularly the elongated shaft 38 thereof. In larger rods, such as 12 to 13 millimeters outside diameter or larger, a single outside diameter may be practiced. However, with smaller outside diameters for the elongated shaft, the slightly larger outside diameter proximal shaft segment 40 helps to accommodate additional features of the subject invention preferably being practiced herewith.

Figure 4D:
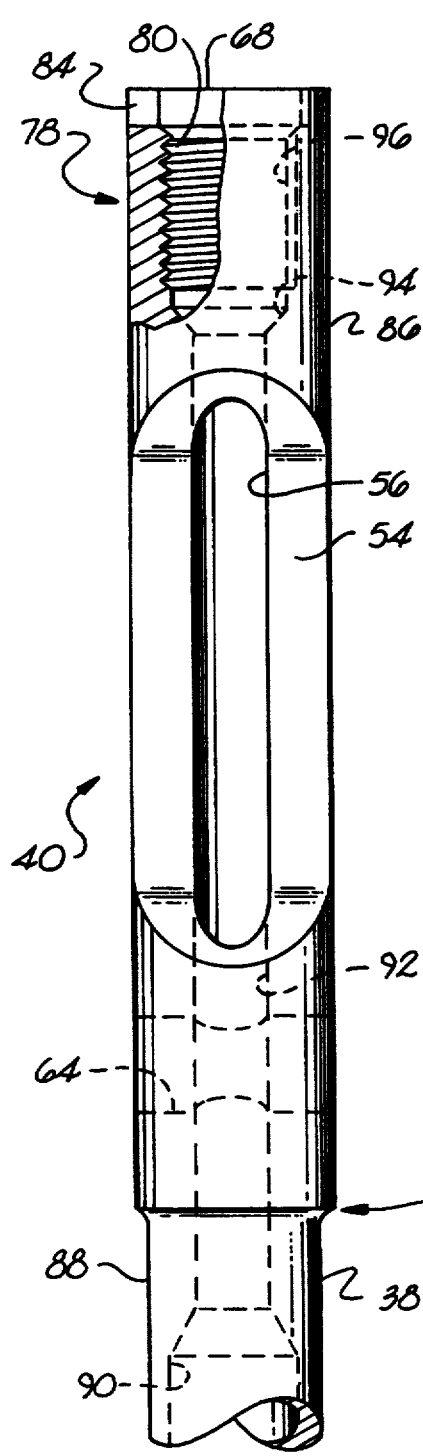
FIGS. 4D and 4E respectively illustrate (in enlargement) the proximal end of an anterior view and a side view (looking in the medial direction) of the first exemplary embodiment of present FIG. 4A.
Figure 4E:
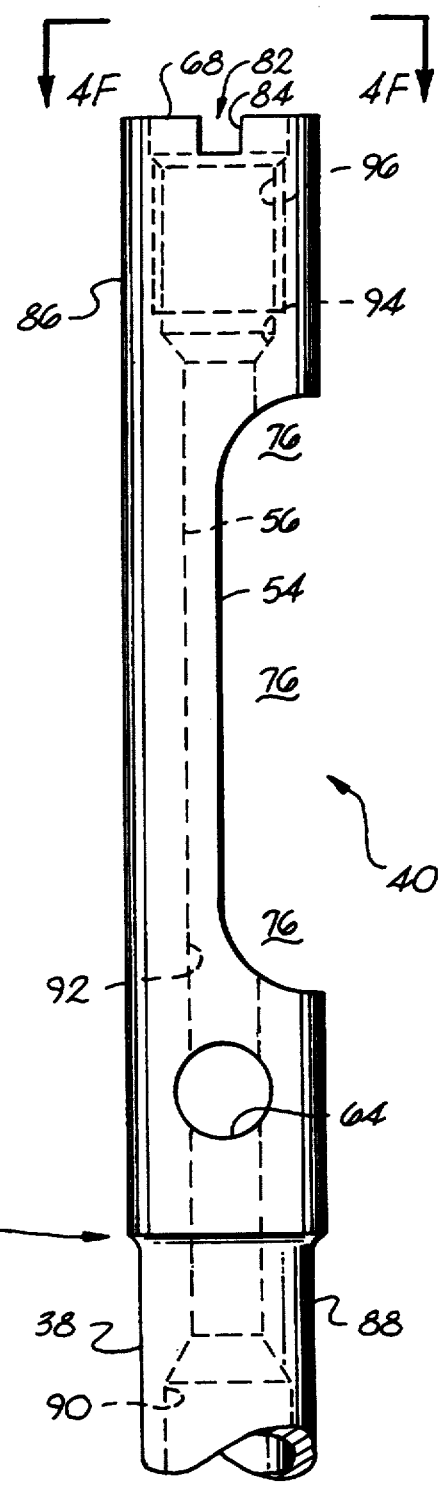
Figure 5B:
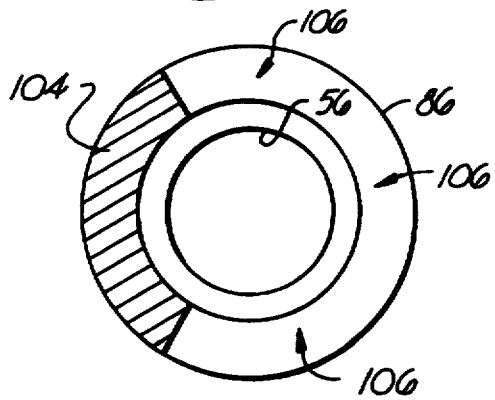
FIG. 5B illustrates a cross-sectional view in the proximal region of the exemplary embodiment of present FIG. 5A, taken along the sectional line 5B—5B indicated therein.
Figure 5A:
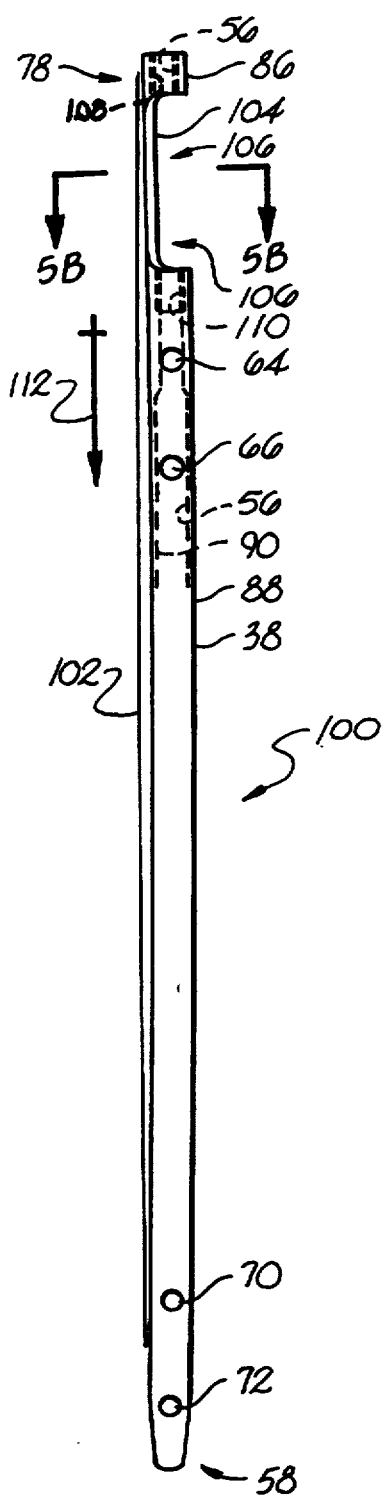
FIG. 5A illustrates a side view (looking in the medial direction) of a second exemplary embodiment of an intramedullary rod in accordance with the subject invention.

FIGS. 4D and 4E particularly illustrate some of the above-referenced attributes of the subject invention in the area of proximal shaft segment generally 40 thereof. Generally speaking, by way of clarification, such proximal shaft segment 40 comprises all portions of rod 36 proximal to the enlarged diameter point approximately 74. The elongated shaft 38 comprises all portions of rod 36 distal to such outside diameter change point 74. The same approximate location in other embodiments constitutes the break point between the elongated shaft and the proximal shaft segment, regardless of whether any change in outside diameter takes place.

More specifically, FIGS. 4D and 4E respectively illustrate (in enlargement) the proximal end region 40 of an anterior view and a side view (looking in the medial direction of the human skeletal right femur) of the first exemplary embodiment 36 of present FIGS. 1 through 4.

While the drawings are not intended as being precisely drawn to scale, they do reflect preferred relative relationships and dimensions among the variously illustrated exemplary components. For example, in an exemplary rod 36, the overall length thereof from distal tip end 58 to proximal end 68 thereof may be about 400 millimeters. In such embodiment, the distance from the most proximal interlocking screw hole 64 to the proximal end 68 may be about 70 millimeters in one preferred embodiment. As represented particularly in present FIG. 3, such an arrangement (and proper seating thereof) results in proximal shaft segment 40 covering (i.e., occupying) substantially all of the femoral hip region (i.e., all portions of the femur even with and proximal to the lesser trochanter generally 34). With such an arrangement, a considerable femoral hip screw passageway generally 76 (see FIG. 4E) is provided. Those of ordinary skill in the art will appreciate and understand that even embodiments of rod 36 may have different specific dimensional characteristics. For example, the overall length of rod 36 may generally fall in a range of from about 300 millimeters to about 500 millimeters, and even fall outside such range for specific embodiments (if necessary to meet a given patient's needs).

Enlarged views of present FIGS. 4D and 4E represent still further present features which may be practiced in accordance with given embodiments of the subject invention. For example, FIG. 4D provides a partial cutaway view adjacent proximal end 68, which represents connection means generally 78 for selectively interconnecting rod 36 with drive components and extraction components for alternate installation and withdrawal, respectively, of rod 36 relative to a receiving femur 20. More particularly, such connection means 78 may comprise internal diameter threads generally 80 formed in at least a portion of the proximal cannulated shaft segment 40. As represented in present FIG. 4D, such threads are formed on the proximal side of the relatively reduced region 54 of rod 36. In such an arrangement, whenever a driving means is coupled with connection means 78, axial rod installation forces may be transmitted through the relatively reduced cross-sectional area region 54. Likewise, axial withdrawal of rod 36 may be obtained through connection of a withdrawal device with connection means 78.

FIG. 4E more particularly illustrates registration means generally 82 which may be associated with proximal end 68 of rod 36, and by which the rotational alignment of rod 36, and hence of the interlocking screw holes 64, 66, 70, and 72 thereof, may be determined, with use of proper instrumentation (such as that presently disclosed herewith in accordance with the subject invention). More specifically, a transverse notch 84 may be provided in proximal end 68, and have a predetermined rotational relationship with reference to the interlocking screw holes, so that location of notch 84 determines (in part) the location of such screw holes. The remaining information necessary to determine the location of such screw holes may be provided in the form of respective predetermined distal distances of such screw holes from proximal end 68, as referenced above.

Figure 4F:
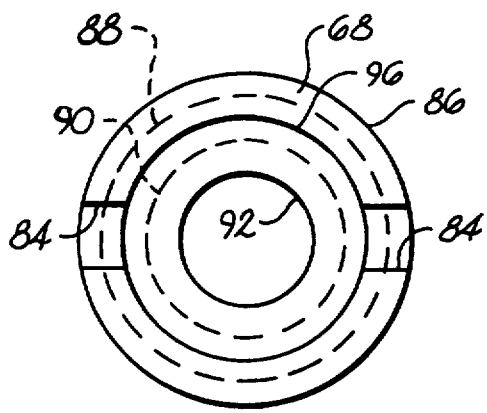
FIG. 4F illustrates a top view of the exemplary embodiment of present FIG. 4E, as seen from the view line 4F—4F indicated therein.

FIG. 4F illustrates a top view of the exemplary embodiment of present FIG. 4E, as seen from the view line 4F—4F indicated therein. Hence, such top view FIG. 4F more fully illustrates both the annular nature of an exemplary cannulated rod and the substantially two part nature of slot 84 across proximal end 68. Utilizing solid line and dotted line illustrations, various outside and inside diameters of the first exemplary embodiment of rod 36 are represented. Generally speaking, the outside diameter 86 of proximal shaft segment generally 40 may fall generally in a range of from about 10 millimeters to about 16 millimeters, and in the lower aspects of such range generally has a slightly larger outside diameter than that of the elongated shaft 38. The slightly smaller outside diameter of such shaft 38 is represented by the dotted line circle 88. Dotted line 90 represents the inside diameter of the elongated shaft 38. See also FIGS. 4D and 4E. As represented in such FIGS. 4D and 4E, the inside diameter 92 throughout much of the proximal shaft segment 40 is the smallest inside diameter in rod 36. As a result, a relative shoulder 94 is formed at the intersection with threaded proximal inside diameter 96. Such shoulder 94 further aids in providing suitable connection means 78 for receipt of axial installation forces.

In one exemplary embodiment having, for example, an outside proximal segment diameter 86 of 14 millimeters, the inside diameter 92 may be about 5 millimeters, while the threaded portion inside diameter 96 is centered on 10 millimeters. In such embodiment, the inside diameter 90 of elongated shaft 38 may be enlarged from diameter 92 to about 9 millimeters, while the outside diameter of elongated shaft 38 may be about 12 millimeters. Other specific dimensions may be practiced, as well as other relative relationships between the respective diameters.

The figures, particularly FIGS. 4D and 4E, further represent that, in a cannulated embodiment, the relatively reduced cross-sectional area 54 is generally constant throughout its designated region. Also, due to the cannulation, an annular region is defined, with the cross-sectional area 54 occupying a predetermined angular portion thereof. As shown by FIGS. 4D and 4E, with such annular region being generally coaxial with the outside diameter 86 of the proximal shaft segment 40, the angular portion of such exemplary embodiment 40, preferably occupies generally about 180 degrees of the annular region. With such an arrangement, the strength of the relatively thin proximal segment or relatively reduced cross-sectional area region 54, is adequate to transmit axial drive forces therethrough to elongated shaft 38. In various embodiments of the subject invention, such angular portion may fall more generally in a range of from about 120 degrees to about 240 degrees of the overall annular region. As the angular portion becomes smaller, particularly as it nears 120 degrees, other connection means are preferred, primarily so as to provide for the transmission of axial drive forces to elongated shaft 38, without requiring axial load bearing on the relatively thin proximal segment.

Figure 4G:
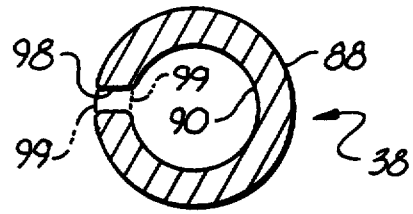
FIG. 4G illustrates a cross-sectional view of the intramedullary rod shaft of the exemplary embodiment of present FIG. 4A, taken along the sectional line 4G—4G indicated therein.

FIG. 4G illustrates still further several different alternative aspects of several specific features for practice in accordance with the subject invention. More specifically, FIG. 4G illustrates a cross-sectional view of the intramedullary rod shaft 38 of the exemplary embodiment of present FIG. 4A, taken along the sectional line 4G—4G indicated therein. Respective outside and inside diameters 88 and 90 of such rod portion are represented. In addition, a lengthwise slot generally 98 is represented, and may be provided along most of the length of elongated shaft 38 for the purpose of relatively increasing flexibility thereof. Such slotted shaft 98 is entirely an optional feature. Shaft 38 is otherwise a generally cylindrical shaft, as represented by dotted lines 99 in FIG. 4G. Other exemplary cross-sectional shapes may be practiced in accordance with this invention, as discussed in greater detail below.

FIG. 5A illustrates a side view (looking in the medial direction of the human skeletal right femur) of a second exemplary embodiment generally 100 of an intramedullary rod in accordance with the subject invention. Such rod 100 may again have primarily an elongated shaft 38, a cannulated inside diameter 56 throughout its length, and optional interlocking screw holes 64, 66, 70, and 72. However, present FIG. 5A represents several alternative features different from those illustrated in present FIGS. 1 through 4.

First, a substantially straight line 102 (an imaginary line) is shown as a point of reference to illustrate that rod 100 may be generally provided with a radius of curvature, primarily in the elongated shaft 38 thereof. Such radius of curvature may generally fall in a range of from about 1 meter to about 3 meters, and more preferably from about 1.1 to about 1.5 meters, so as to match the known natural curvature of a patient's femur. In addition, for those embodiments which make use of a rod radius of curvature, an intended rotational relationship is established relative to the femur, thereby establishing the intended relative position (for example, posterior, anterior, or the like) of the relatively thin proximal segment provided. Present FIGS. 1 through 4 represent no particular radius of curvature, but such may be practiced so that the resulting relatively reduced cross-sectional area region 54 is always intended to be in a relatively posterior location to provide a relatively anterior passageway for femoral hip screws 42, 44, and 46.

Present FIG. 5A is similar to present FIGS. 1 through 4 in that it shows a relatively intended posterior location of a relatively reduced cross-sectional area region or thin proximal segment 104 thereof. Such relatively thin proximal segment 104 results in the creation of a complementary femoral hip screw passageway 106. In other words, present FIG. 5B illustrates a cross-sectional view in the proximal region of the exemplary embodiment 100 of present FIG. 5A, taken along the sectional line 5B—5B indicated therein, and representing an angular portion 104 of only approximately 120 degrees of the complete annular region defined between cannulated inner diameter 56 and proximal shaft segment outside diameter 86. As shown, such arrangement creates a substantial complementary passageway 106 covering an angular portion of approximately 240 degrees of the total available annular region.

As a result, it is preferred for embodiments such as FIG. 5A that the connection means generally 78 include internal diameter threads formed in both a proximal side 108 relative thin proximal segment 104 and a relative distal side 110 thereof. With such an arrangement, a threaded driving means may be connected down through proximal region 108, passageway 106, and threadably seated into the relative distal side threads 110. With such a resulting arrangement, axial rod installation forces (in the direction of arrow 112) are not transmitted through the relatively reduced cross-sectional area region or thin proximal segment 104. Instead, forces are more directly applied to rod shaft 38. By providing such a form of connection means generally 78, the relatively thin proximal segment 104 is able to be made even relatively thinner in relation to the full outside diameter 86 in such proximal shaft segment.

Those of ordinary skill in the art should understand and appreciate that further embodiments of the subject invention may provide the relatively thin proximal segment 104 in a relatively anterior location, given the intended orientation of the intramedullary rod relative to a receiving femur, so that femoral hip screws may be received in a relatively posterior position. The same alternative positioning arrangement may be practiced, for example, in conjunction with the exemplary embodiment of rod 36 of present FIGS. 1 through 4, and is in fact so represented in present FIGS. 6A and 6B.

Figure 6A:
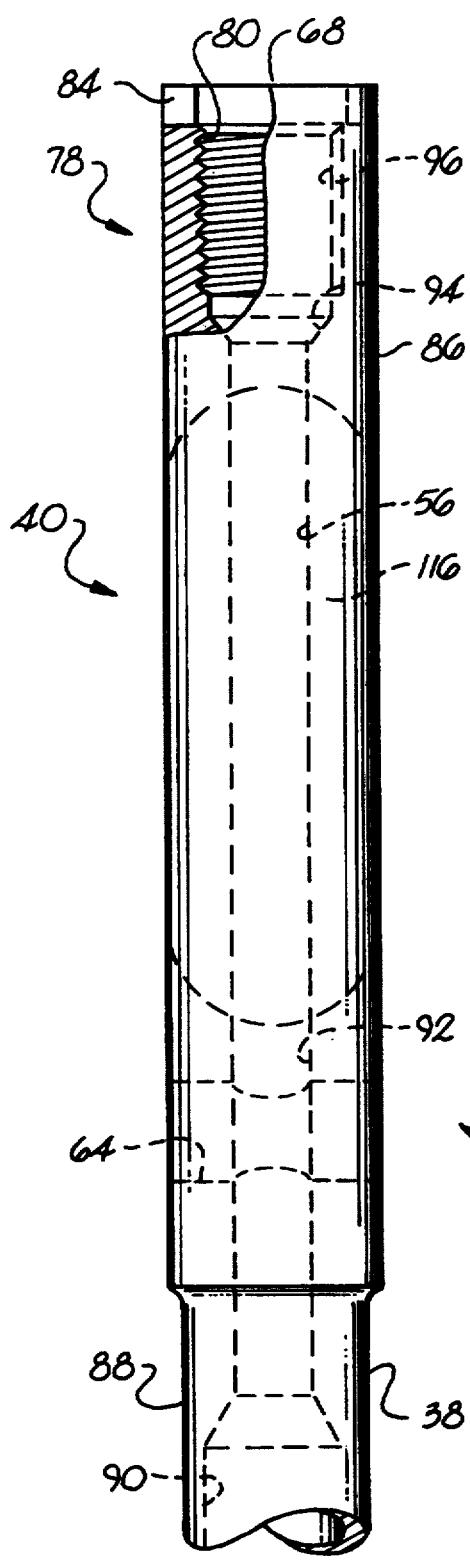
FIGS. 6A and 6B respectively illustrate (in enlargement) the proximal end of an anterior view and a side view (looking in the medial direction) of a third exemplary embodiment of an intramedullary rod in accordance with the subject invention.
Figure 6B:
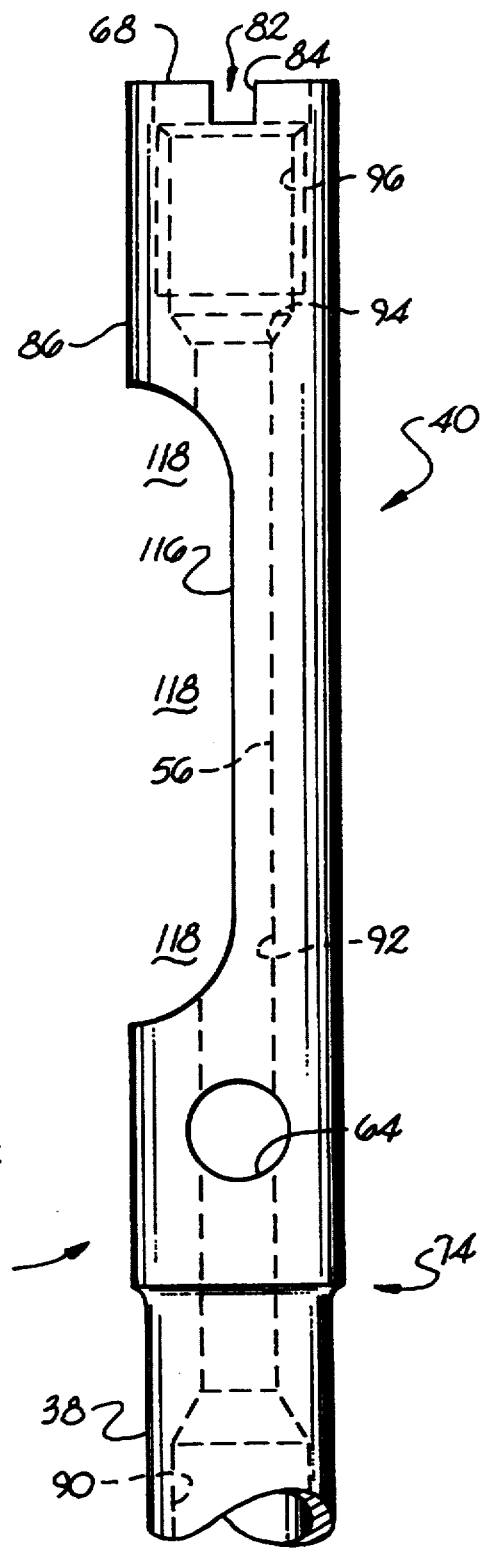

More specifically, present FIGS. 6A and 6B respectively illustrate (in enlargement) the proximal shaft segment 40 of an anterior view and a side view (looking in the medial direction of a human skeletal right femur) of a third exemplary embodiment generally 114 of an intramedullary rod in accordance with the subject invention. Those of ordinary skill in the art will readily appreciate that FIGS. 6A and 6B constitute in essence the reverse image of present FIGS. 4D and 4E, and vice versa. Hence, like reference characters are utilized so as to eliminate the need for lengthy detailed discussion. Rather, an anterior position for relatively thin proximal segment generally 116 is illustrated in place of the relatively thin proximal segment 54 of present FIGS. 4D and 4E. Likewise, present FIG. 6B illustrates a relatively posterior location for a femoral hip screw passageway 118 of exemplary embodiment 114, in place of the generally anterior passageway 76 of present FIG. 4E. Remaining present features of FIGS. 6A and 6B correspond with previously discussed features of present FIGS. 4D and 4E, and are marked with reference characters accordingly.

Present FIG. 7A illustrates a side view (in the medial direction of a human skeletal right femur) of yet a fourth exemplary embodiment of an intramedullary rod generally 120 in accordance with the subject invention. The distinctive feature primarily represented by such figure relates to yet a further exemplary embodiment of a relatively thin proximal segment or relatively reduced cross-sectional region generally 122 thereof. The arrangement is further illustrated by FIG. 7B, representing a cross-sectional view in the proximal region of the exemplary embodiment 120 of present FIG. 7A, taken along the sectional line 7B—7B indicated therein.

As shown by FIG. 7B, the relatively reduced cross-sectional area actually occupies what may be described as a partially annular position, i.e., two distinct angular portions 124 and 126 of the full annular region defined between proximal shaft segment diameter 86 and inside diameter 56 thereof.

Similar to the construction of present FIG. 5A, respective threaded regions 108 and 110 are provided proximally and distally to the relatively thin proximal segment 122 so as to comprise threaded connection means for rod 120. At the same time, it will be further apparent to those of ordinary skill in the art from viewing both present FIGS. 7A and 7B that a substantial femoral hip screw passageway generally 128 is formed between the opposing annular segments 124 and 126. In general, each such annular segment 124 and 126 comprise about 120 degrees angular coverage of the full annular region available between proximal shaft segment outside diameter 86 and cannulation inside diameter 56 thereof. The segments 124 and 126 may fall in more of a range generally comprising from about ¼ to about ⅓ each of the full annular region.

FIG. 8A illustrates (in enlargement) a side view of a proximal end portion of yet a further exemplary embodiment of an intramedullary rod generally 130 in accordance with the subject invention. Primarily, the rod 130 differs from previously illustrated embodiments in that the relatively reduced cross-sectional area or relatively thin proximal segment thereof generally 132 occupies a central or center post position. In a cannulated embodiment, such center post arrangement 132 includes respective outside and inside diameters 134 and 136. FIG. 8B illustrates a cross-sectional view in the proximal region of such exemplary embodiment generally 130 of present FIG. 8A, taken along the sectional line 8B—8B indicated therein.

A still further embodiment of exemplary connection means generally 78 is shown by the specific configuration of proximal end inside diameter threads generally 138 formed in a portion of the rod adjacent to proximal end 68 thereof. As shown, such threads 138 have a substantially larger inside diameter than the cannulation inside diameter generally 140 in the relatively thin proximal segment 132, resulting in a substantial interior shoulder 142 between such respective inside diameters. Other present features may be practiced, such as registration or alignment proximal end slot 84 (as represented), or a given radius of curvature for rod 38 (represented generally by present FIG. 5A), or the use of interlocking screw holes along the rod, as represented by present FIG. 4A. Certain features may be utilized in still further capacities and locations, such as the relatively moved exemplary illustration of alignment slot 84 shown in the cross-sectional view of present FIG. 8B. All such variations and different combinations, as would be understood by those of ordinary skill in the art, are intended to come within the spirit and scope of the present invention by virtue of present reference thereto.

FIG. 9A illustrates a side view (in the medial direction of a human skeletal right femur) of a general illustration of an exemplary intramedullary rod generally 144 in accordance with the subject invention, and representative of present optionally used variations in the shaft section thereof. With the exception primarily of the specific shape of the shaft cross-sectional area thereof, the features of exemplary rod 144 are generally about the same as those of exemplary rod 36 of present FIG. 4A. FIG. 9B more fully illustrates the differences between embodiments 36 and 144, by representing a cross-sectional view of the shaft 146 which has an outside diameter 148 which may broadly be referred to as being fluted. Two opposing flutes or depressions generally 150 and 152 are represented, and contrast with a generally cylindrical inside diameter 154. However, in some embodiments, it may be practiced that the inside diameter 154 is formed, such as with cold rolling, or the like so that the inside diameter 154 actually matches the shape of the outside diameter 148.

In addition to the cylindrical, slotted, and fluted embodiments discussed above, still further cross-sectional shaft shapes may be practiced. For example, present FIGS. 9C and 9D illustrate respective alternative cross-sectional rod shaft embodiments 156 and 158 which may be practiced in place of the exemplary embodiment of present FIG. 9B. Moreover, such features may be utilized in combination with other present exemplary proximal end portions and other features of the exemplary intramedullary rods disclosed herewith.

More specifically, FIG. 9C represents an outside diameter 160 which is fluted (including three flutes generally 162, 164, and 166), and a generally circular inside diameter 168. Again, inside diameter 168 may alternatively be formed in the same shape as outside diameter 160.

The FIG. 9D embodiment illustrates an outside diameter generally 170 having fluting comprising a total of four separate flutes generally 172, 174, 176, and 178. A relatively cylindrical inside diameter 180 may be practiced, or other shapes may be utilized, particularly those matching the outside diameter generally 170.

In the embodiments discussed above, the proximal shaft segment of each respective embodiment is preferably integrally formed with its corresponding elongated shaft, in axial alignment therewith. Present FIGS. 10A, 10B, and 10C illustrate a sixth rod embodiment generally 182 in which the proximal shaft segment generally 184 and the elongated shaft generally 186 comprise respective, axially matably members which may be joined together with joining means generally 188 in accordance with the present invention.

Figures 10A, 10B, 10C:
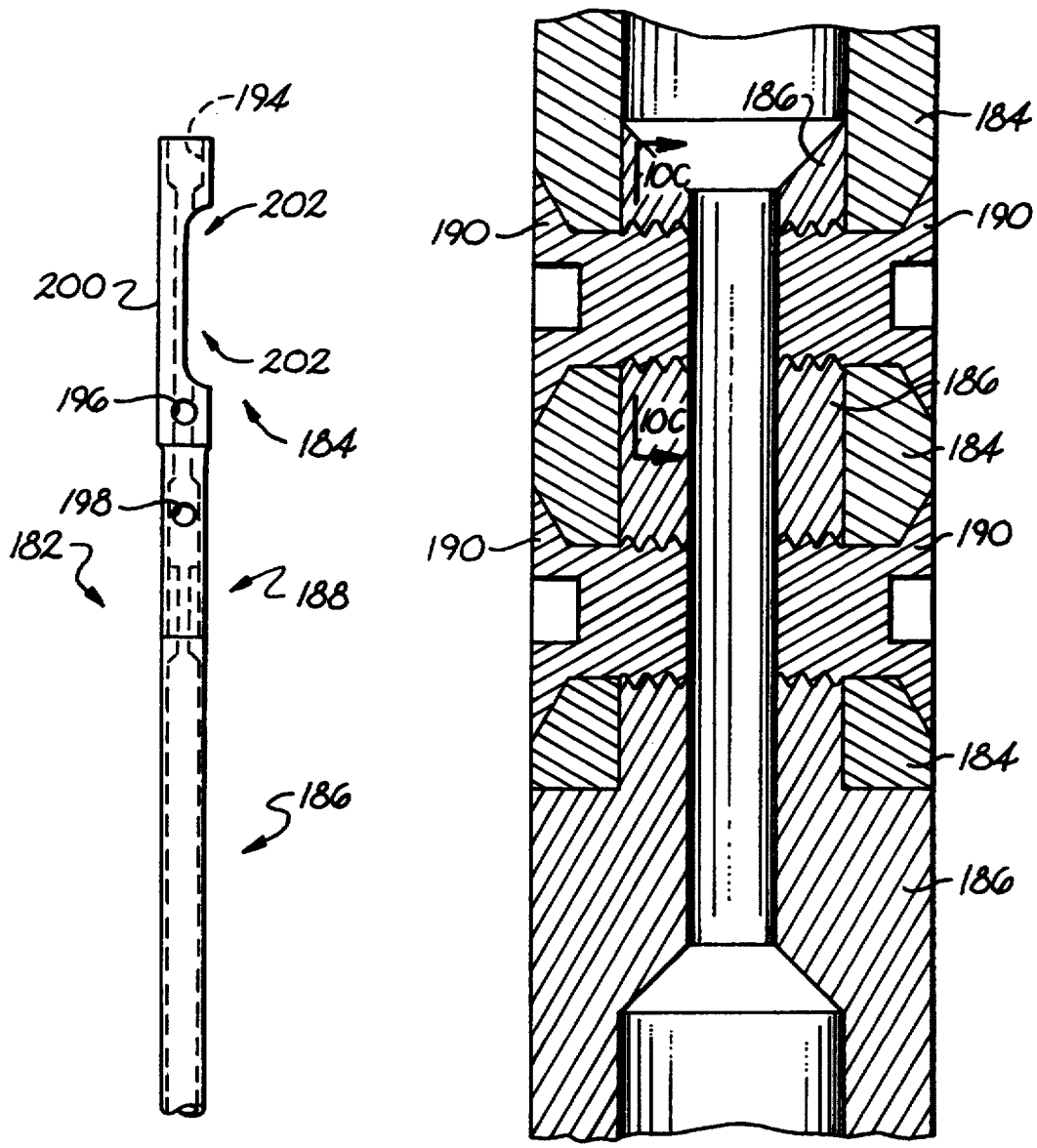
FIG. 10A illustrates a partial side view (in the medial direction) of a sixth exemplary embodiment of an intramedullary rod in accordance with the subject invention, particularly having interchangeable features for the proximal end portion thereof.
FIG. 10B illustrates an enlarged cross-sectional view of the proximal end portion interchangeable features of the present exemplary embodiment of FIG. 10A.
FIG. 10C represents a cross-sectional view of an exemplary locking bolt as used in the exemplary embodiment of present FIG. 10B, taken along the sectional line 10C—10C indicated therein.

More specifically, FIG. 10A illustrates a partial side view (in the medial direction of a human skeletal right femur) of the exemplary rod 182, particularly having interchangeable features for the proximal end portion 184 thereof. FIG. 10B illustrates an enlarged cross-sectional view of such proximal end portion generally 184 of the embodiment of FIG. 10A. FIG. 10C specifically represents a cross-sectional view of an exemplary joining means feature (for example, a locking bolt) as used in the exemplary embodiment of present FIG. 10B, taken along the sectional line 10C—10C indicated therein.

The enlarged view of present FIG. 10B illustrates how the joining means generally 188 may axially join the respective proximal shaft segment generally 184 and the elongated shaft 186 in mated axial arrangement. As shown by alternately directed diagonal lines, the respective members 184 and 186 are preferably telescopically related to one another and held together, for example by such as a plurality of locking bolts 190. FIGS. 10B and 10C are representative of preferred exemplary set screws, such as so-called "prevailing-torque" locking fasteners. As shown in FIG. 10C, the threaded shaft 192 may have deformed threads or otherwise contoured thread profiles so as to, in essence, jam into place for a very secure fit. Other forms of locking fasteners, set screws, lock nuts, pins, or other forms of joining means may be practiced. For example, the members 184 and 186 may be threadably joined together or brought together with matably aligned splines, or other forms of actual joining, so long as a connection of adequate strength is provided.

Those of ordinary skill in the art will appreciate that the purpose of an embodiment such as FIGS. 10A, 10B, and 10C is to permit the use of a particular proximal shaft segment with a predetermined selected shape for the relatively reduced cross-sectional area region thereof, so as to provide a treating physician with a selected location for the femoral hip screw passageway customized for the femoral neck or hip fracture treatment of a given patient. The illustration of present FIG. 10A represents use of a cannulated embodiment having a cannulation inside diameter 194, relatively proximal interlocking screw holes 196 and 198, and a generally posteriorly located relatively thin proximal segment 200. From the foregoing discussion, it will be understood that such arrangement results in a generally anterior femoral hip screw passageway 202. It will be apparent that the predetermined selected shape and location of such passageway may be selected by providing a relatively reduced cross-sectional area of predetermined shape as occupying one of a posterior, anterior, central, or partially annular position, as discussed in the embodiments of FIGS. 1 through 9.

Still further, other alternative arrangements may be practiced, including configurations different from those expressly illustrated. For example, different angular portions of the annular region for relatively thin proximal segment 200 may be practiced, as in the above embodiments. Also, different rotational alignments may be practiced. For example, in FIG. 7A, the femoral hip screw passageway 128 is aligned with the direction of interlocking screw holes 64, 66, 70, and 72. The annular segments 124 and 126 could be in positions rotated therefrom, such as by 90 degrees, so that the passageway 128 is instead transverse to the interlocking screw holes. Other relatively axially rotated arrangements could be practiced, either in the modular embodiment of present FIGS. 10A through 10C, or in an integral embodiment, and all such modifications and variations are intended to be covered by the present invention.

FIGS. 11A through 11E represent a still further aspect of certain "modular" features which may be practiced in accordance with the subject invention. More specifically, FIG. 11A illustrates (in enlargement of a proximal portion generally 204) a side view (in the medial direction of a human skeletal right femur) of a seventh exemplary embodiment of an intramedullary rod generally 206 in accordance with the subject invention, particularly having modular components, with the selected addition of which converts the intramedullary rod 206 from one type proximal end to another type proximal end. FIGS. 11B, 11C, and 11D illustrate respectively a side view (in the medial direction of a human skeletal right femur), an anterior view, and a bottom view of a modular component generally 208 in accordance with this aspect of the subject invention.

FIG. 11A represents a generally posterior relatively thin proximal segment generally 210, similar to the exemplary constructions of present FIGS. 1, 4E, 9A, and 10A. As illustrated, the modular element 208 has a contour which is complementary to that of the femoral hip screw passageway defined by relatively thin proximal segment 210. So configured, modular element 208 fills in the femoral hip screw passageway whenever attached to such proximal shaft segment 204.

FIG. 11E illustrates a cross-sectional view of an exemplary locking bolt (i.e., modular element attachment means) such as may be used in the exemplary embodiment of present FIG. 11A, taken the sectional line 11E—11E indicated therein, for attaching modular element 208 to the proximal shaft segment 204. The locking bolt 212 may include threaded shaft segment 214 of a prevailing torque type (see FIG. 10C and related discussion) which deforms or jams in the attachment screw holes 214. Those of ordinary skill in the art will understand that such attachment is done prior to implantation of intramedullary rod 206, which may further have cannulation inside diameter 216, threaded connection means 218, a registration slot 220, an interlocking screw hole 222, and other features of other embodiments herewith. Various such combinations may be practiced in conjunction with use of a modular component 208, and such component may take on different shapes so as to fill differently shaped femoral hip screw passageways.

In addition to the attachment means screw holes 224 formed in modular element 208, partial screw hole openings 226 may be formed therein, as follows. Certain standard "recon" intramedullary rods or nails include femoral hip screw holes placed at specific angles therein, for the upwardly angled seating of hip screws, similar to the seating of hip screws represented in present FIGS. 1 through 3. Therein, such screws 42, 44, and 46 enter from a generally lateral side and proceed at approximately a 45 degree angle from the proximal direction, upwardly through the femoral neck and into the femoral head. The exemplary embodiment of present FIGS. 11A through 11E represent such "recon" type holes formed by respective hole components 226 of the modular component 208 and hole portions 228 formed in relatively thin proximal segment 210. Those of ordinary skill in the art will understand that other combinations and placements of such openings may be provided in accordance with such modular component embodiment of the subject invention, and others. Likewise, various features such as countersunk screw heads and the like, as would be apparent to those of ordinary skill in the art, may be practiced with the foregoing embodiment.

The foregoing description relates primarily to specific examples and variations of intramedullary rods which may be practiced in accordance with the subject invention. The remainder of this description primarily relates to various devices for use with the subject intramedullary rods, resulting in various treatment systems and methods in accordance with this invention, including installation and withdrawal devices and methodology. For example, one treatment system in accordance with the subject invention for the treatment of ipsilateral fracture patterns of the femoral hip and shaft may include a femoral intramedullary rod (such as one of the above-described embodiments), driving means for installation of such rod in a receiving femur, a plurality of interlocking screws for securing the rod, interlocking screw guide means for alignment of such interlocking screws during seating thereof, and at least one femoral hip screw for seating in the passageway defined therefor with the intramedullary rod in accordance with this invention. The following discussion with reference to present FIGS. 12-19 discusses such arrangement, and others, as well as present methodology.

Figure 12:
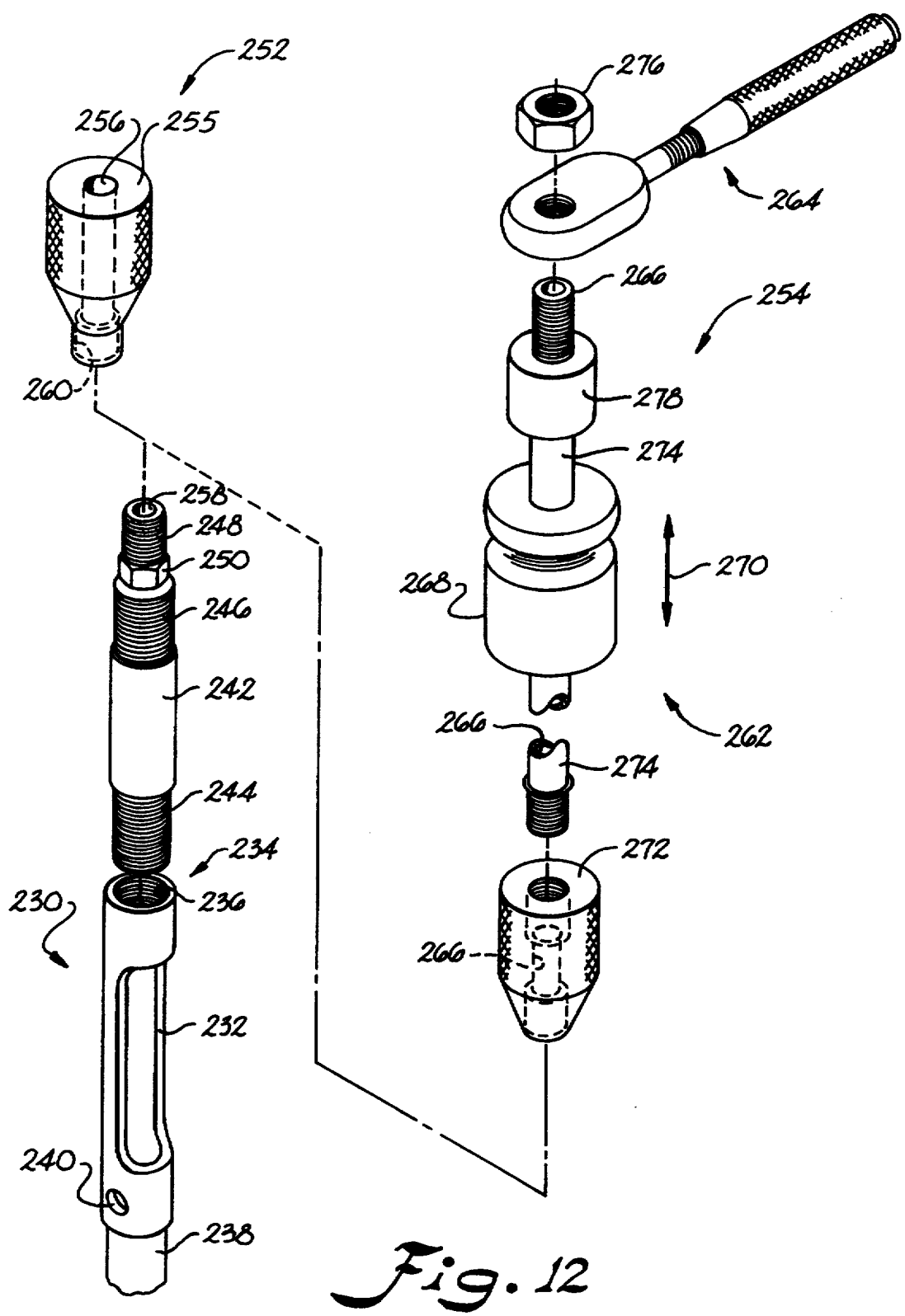
FIG. 12 illustrates an isometric and exploded view of alternative installation arrangements in accordance with the subject invention, and particularly adapted for use with intramedullary rods of the present invention.
Figure 13:
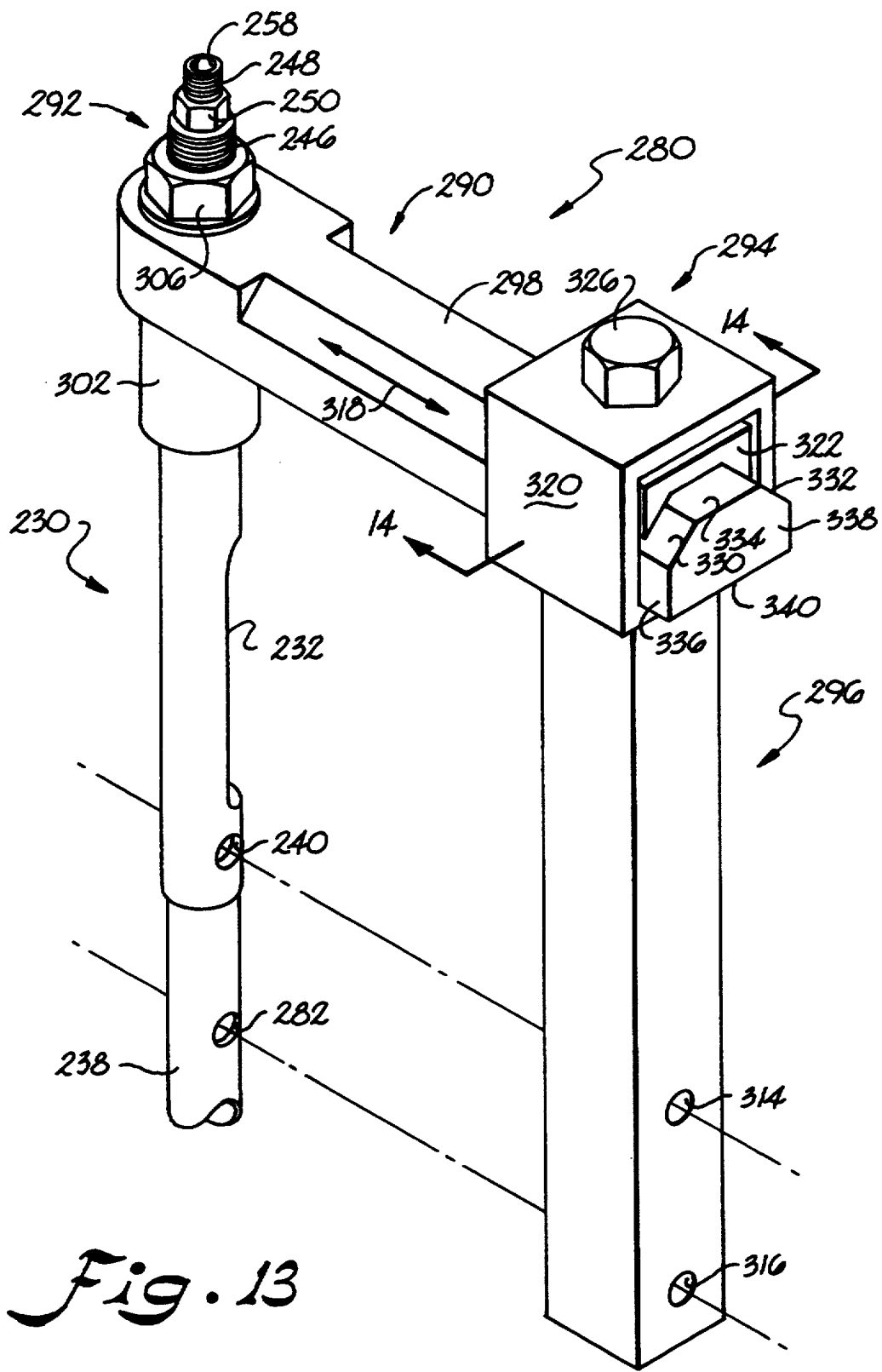
FIG. 13 illustrates an isometric view of an assembled proximal screw hole targeting apparatus in accordance with the subject invention, particularly adapted for use with intramedullary rods of the present invention.
Figure 14:
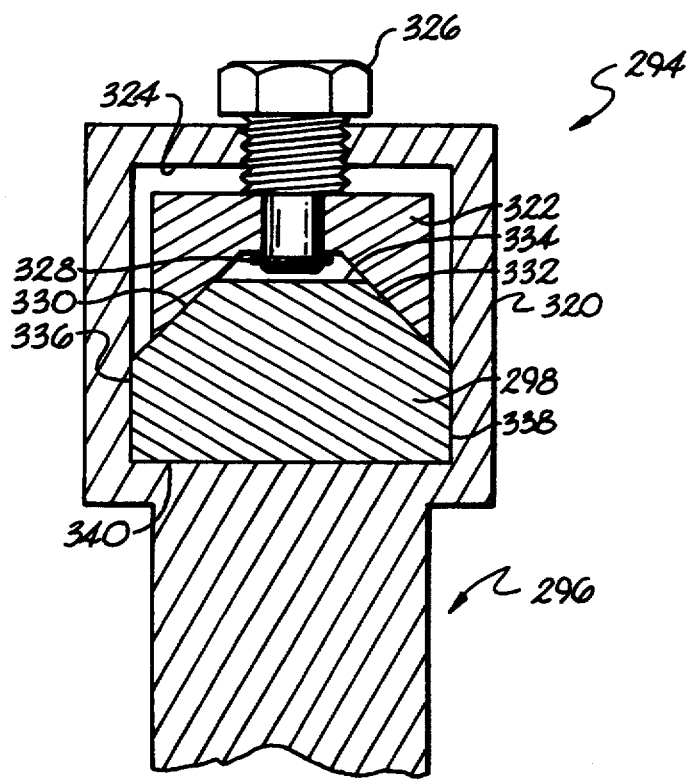
FIG. 14 illustrates an enlarged cross-sectional view of clamp plate features for a proximal interlocking screw targeting arm in accordance with the subject invention, in accordance with the exemplary embodiment of present FIG. 13, taken along the sectional line 14—14 indicated therein.
Figure 16:
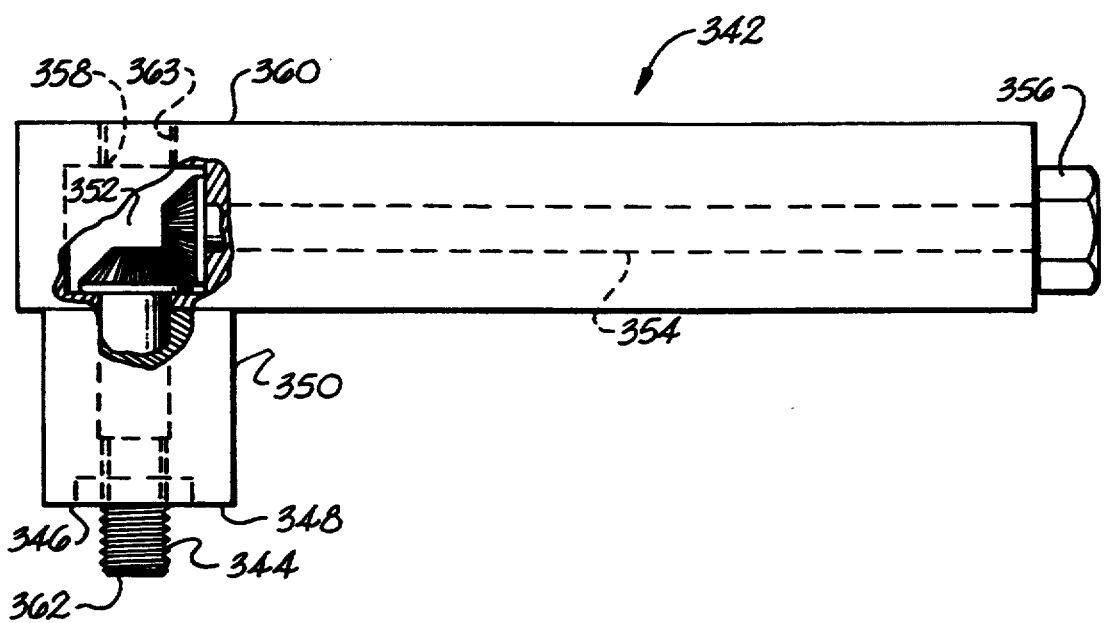
FIG. 16 illustrates a side elevational view, with partial cutaway, of a rotational position control arm with a 90 degree drive feature for locking bolts, in accordance with additional features of the subject invention, particularly adapted for use with intramedullary rods in accordance with the present invention.
Figure 15:
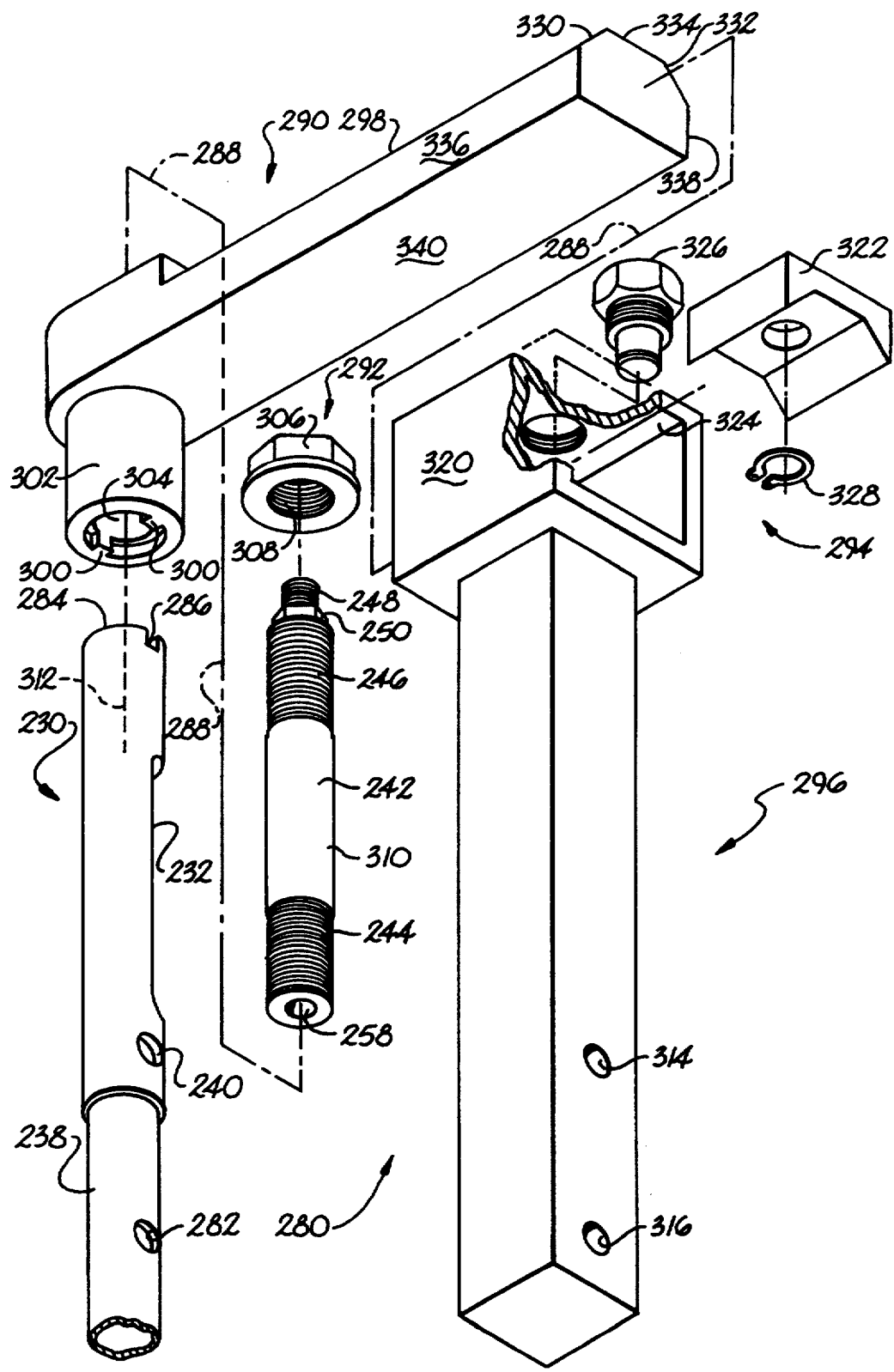
FIG. 15 illustrates an isometric exploded view of the exemplary apparatus of the subject invention as illustrated in assembled form in present FIG. 13.
Figure 17:
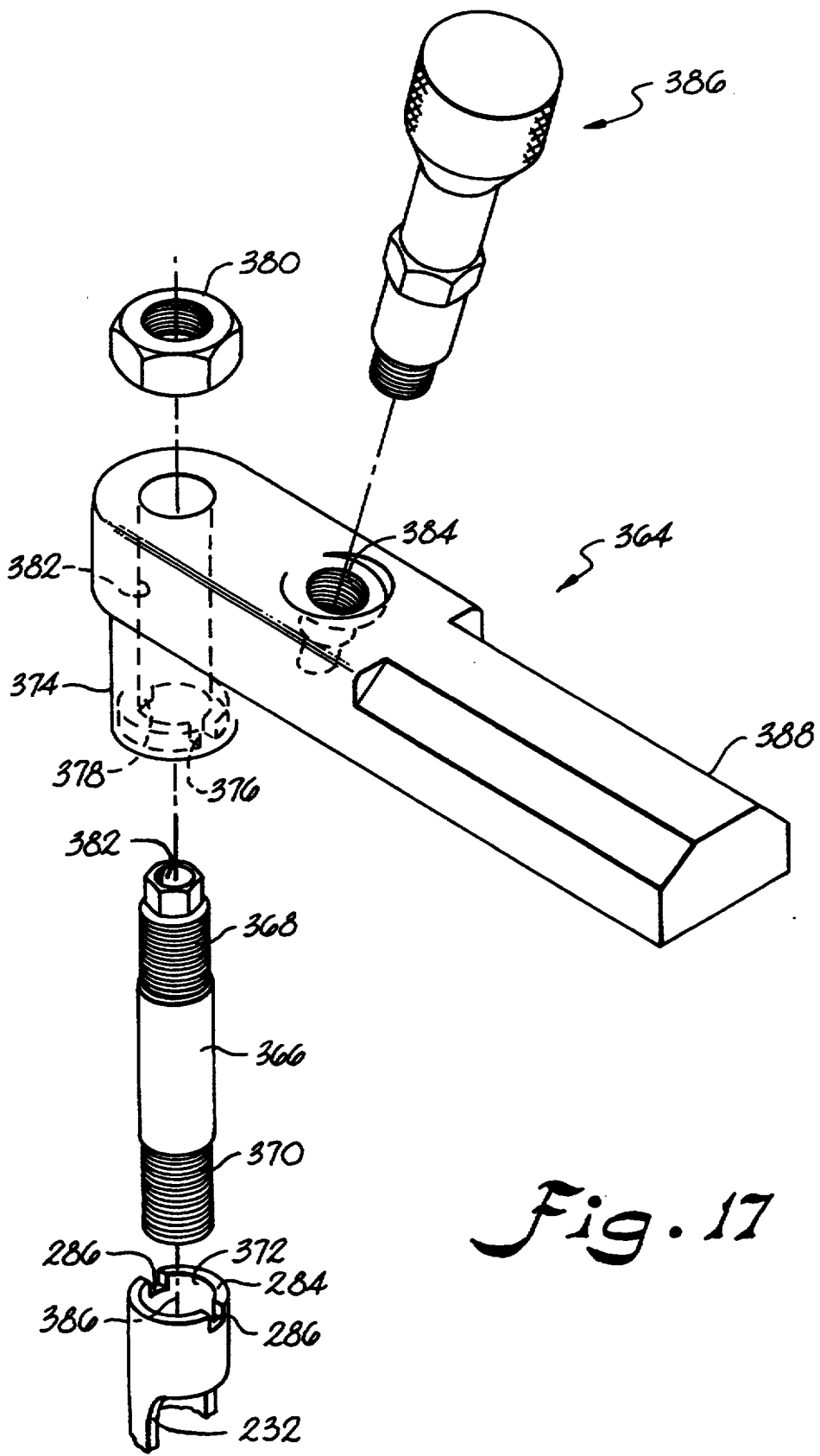
FIG. 17 illustrates an isometric exploded view of an alternative embodiment of a laterally extending clamp plate support (for use in place of the embodiment of present FIG. 13), and also having a repositioned hammer block arrangement.
Figure 18:
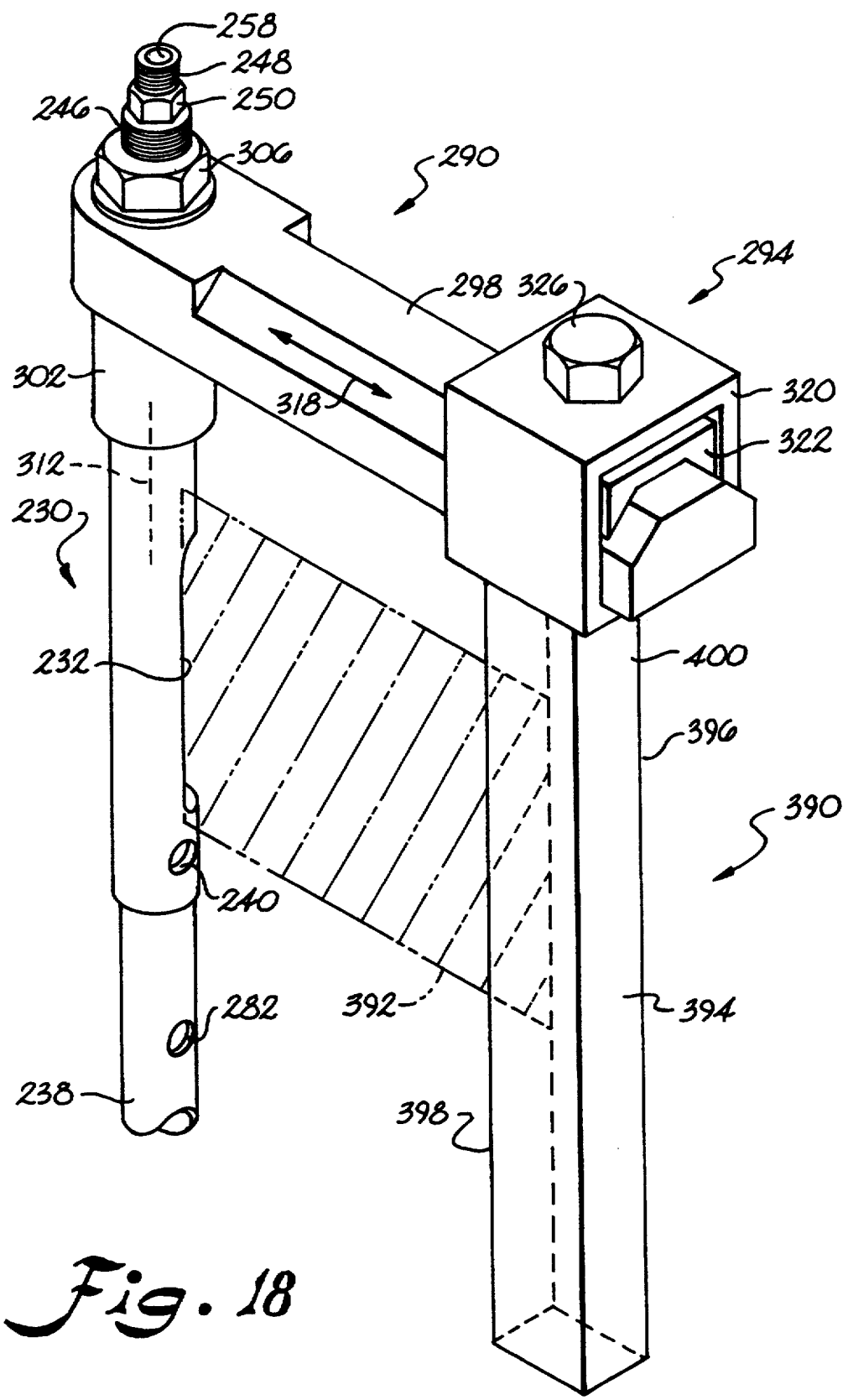
FIG. 18 illustrates an isometric view of a further exemplary embodiment in accordance with the subject invention, illustrating alternative features to those of present FIG. 13, and particularly representing a neck or hip screw placement guide arm for use in accordance with the subject invention, particularly adapted for use with intramedullary rods in accordance with the present invention.
Figure 19:
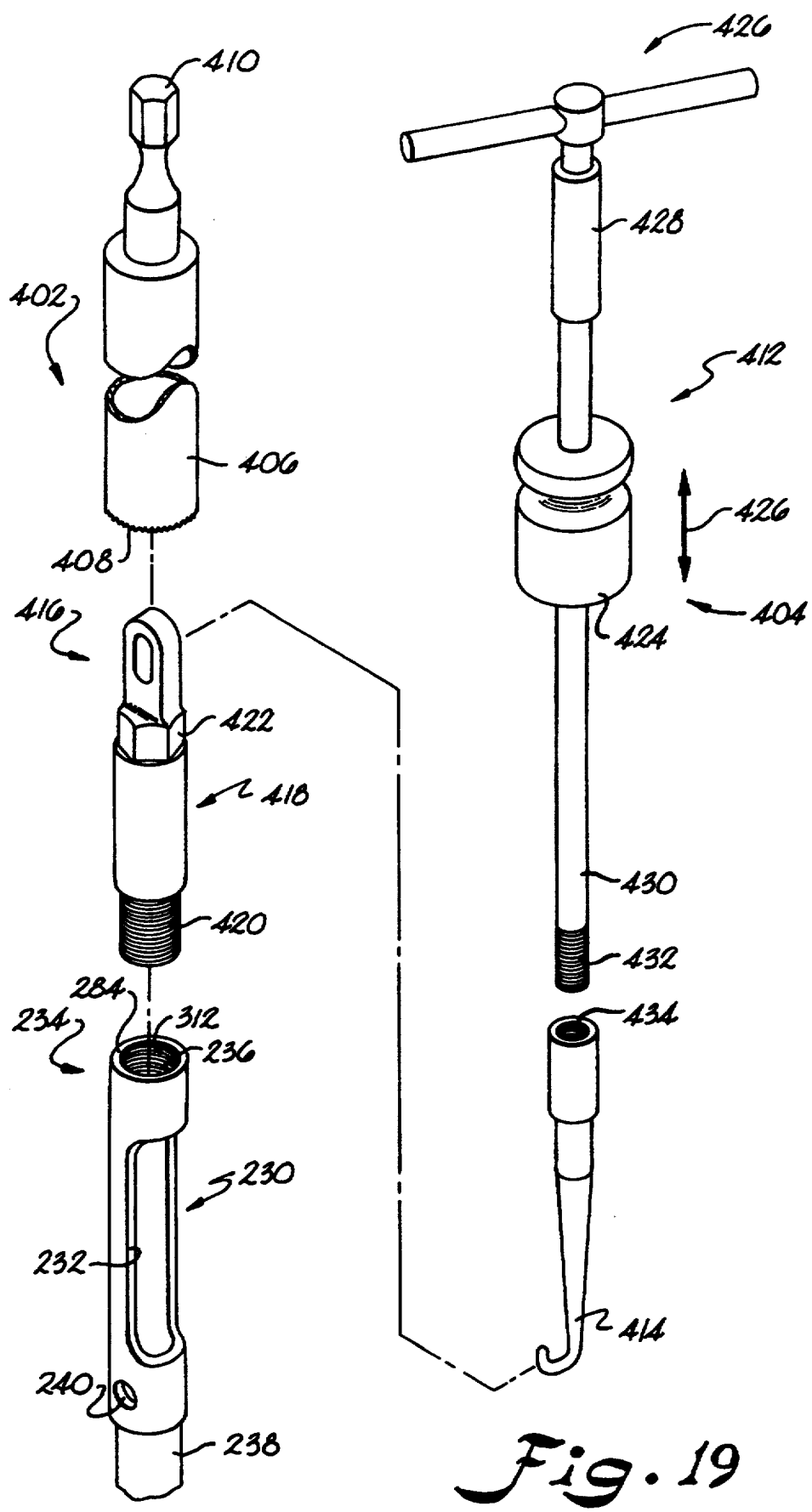
FIG. 19 illustrates an isometric exploded view of a proximal end over-reamer in accordance with the subject invention for use during extraction of intramedullary rods in accordance with the present invention, and further illustrates elongated slide hammer rod removal features for use in accordance with the subject invention during such extraction.

More specifically, FIG. 12 illustrates various alternative driving arrangements for installing an intramedullary rod in accordance with the present invention, while FIG. 13 illustrates exemplary interlocking screw guide means of the present invention. FIG. 14 shows a cross-sectional detail of a portion of such interlocking screw guide means, while FIG. 15 shows an exploded representation of the entire guide means. FIG. 16 represents an exemplary 90 degree drive for use in practicing the present invention, while FIG. 17 illustrates one alternative embodiment of a portion of the FIG. 13 device. FIG. 18 illustrates yet another alternative to portions of the features of FIG. 13, so as to provide an alignment guide for seating of the femoral hip screws, while FIG. 19 represents various features and methodology for the ultimate withdrawal of an intramedullary rod from a healed femur.

Those of ordinary skill in the art will appreciate that the following devices and methodology may be practiced with any of the foregoing, and other, embodiments of the present intramedullary rod. For purposes of example only, an intramedullary rod proximal shaft segment generally 230 is shown in FIG. 12, similar to the embodiment of present FIGS. 1 and 4A. Briefly, such proximal shaft segment 230 has a relatively thin proximal segment 232 which includes connection means generally 234 comprising cannulation inside diameter threads 236, and which shaft segment 230 is connected with an elongated shaft 238 distally therefrom (partially shown), and which further includes a single representative interlocking screw hole 240.

A further threaded element 242 may be provided for axially connecting with rod connection means threads 236 via threads 244. Member 242 comprises, in essence, a modular component for the additional connection thereto of other removably operative devices, which may variously connect to threads 246 thereof (having a relatively larger outside diameter) or proximal threads 248 thereof (having a relatively smaller outside diameter and also having a stop hex coupling 250 or similar integrally formed at the base thereof).

As further shown by FIG. 12, various alternative driving means generally 252 and 254 may be removably operatively associated with the rod proximal end connection thread means 236 (such as via member 242) for selectively driving the intramedullary rod shaft 238 to a desired predetermined depth into a receiving fractured femur, with the result that the rod proximal shaft segment 230 is received in the femoral hip region. In one embodiment, the driving means 252 may comprise a threaded hammer block 255 for use with a free-hand hammer (not shown). Such hammer block 255 has a cannulation passageway 256, which mates with a similar cannulation passageway 258 of extension member 242. An internal diameter thread connection 260 (or some other equivalent means) may be provided for connecting hammer block 255 to the extension member 242. In such position, a fully cannulated device is provided so that the intramedullary rod may be seated over a guide wire, in accordance with general installation procedures with which those of ordinary skill in the art are familiar, without additional detailed discussion thereof.

The alternative embodiment of present driving means 254 represents a threaded slide hammer means generally 262 and attached handle generally 264. Such arrangement also makes use of a cannulation passageway generally 266 along its full length so that the rod may be driven over the guide wire, or possibly over reaming guides, or other similar devices. The threaded slide hammer means includes a mass 268 which may be manipulated for alternate travel along the axial direction of double-headed arrow 270. The threaded slide hammer means 262 further includes a drive type member 272, relatively similar to hammer block 255, and against which mass 268 is axially moved for striking the intramedullary rod shaft 238 in a distal direction.

Those of ordinary skill in the art will appreciate from the illustration of present FIG. 12 the various threaded couplings which may be practiced, including the coupling between members 272 and axial support shaft 274, as well as the locking nut coupling 276 which may be used in conjunction with handle 264. An upper stop member 278 may be formed in a fixed position along shaft 274. Use of handle 264 facilitates driving of the rod shaft 238, while also permitting to a certain extent the rotational manipulation thereof. Variations to these arrangements may be practiced, as will be understood by those of ordinary skill in the art.

Those of ordinary skill in the art are already familiar with various guide wire and reaming techniques which may be practiced as part of installation procedures for conventional intramedullary rods. One advantage of the present intramedullary rod is that it may be utilized with such procedures already familiar to many practicing orthopedic physicians. Another present advantage is the additional use of equipment disclosed herewith, such as the interlocking screw guide means of present FIG. 13, which further simplifies operations, as discussed hereinafter.

In general, once an intramedullary rod is seated, interlocking screws (if used) are put in place. Present FIGS. 13 through 15 illustrate interlocking screw guide means generally 280 in accordance with the subject invention, for the targeting and alignment of relatively proximal interlocking screw holes 240 and 282. FIG. 13 illustrates an isometric view of an assembled proximal screw hole targeting apparatus generally 280 in accordance with the subject invention, particularly adapted for use with present intramedullary rods, while FIG. 15 illustrates an isometric exploded view of such exemplary apparatus 280.

In general, interlocking screw holes 240 and 282 are situated a predetermined or known distal distance (respectively) from proximal end 284 (FIG. 15) of the intramedullary rod. In addition, as discussed above with reference to various of the figures, a registration means slot 286 or other form of alignment may be utilized for indicating the relative rotational position of screw holes 240 and 282. Those of ordinary skill in the art will understand (such as from exemplary FIGS. 1 and 3) that the proximal end 284 of the intramedullary rod remains close to the outer surface of the femur, so that access may be had to registration slot 286. The dotted continuation line 288 shown throughout FIG. 15 represents desired interconnection of the elements comprising interlocking screw guide means 280, as discussed in detail hereinafter.

Such interlocking screw guide means 280 may variously comprise a combination of different respective devices and elements, such as rotational position control arm means generally 290, securement means generally 292, selectively operable clamping means generally 294, and targeting arm means generally 296.

More specifically, the rotational position control arm means generally 290 may in one exemplary embodiment comprise a member which is removably operatively associated with the rod proximal end registration means 286 and which extends generally laterally therefrom via a lateral extension arm 298. When so extended, arm 298 is in rotational alignment with the rod relatively proximal interlocking screw hole or holes 240 and 282. A pair of tabs 300 or other correspondingly mating elements, may be provided for use in conjunction with registration slot 286. As shown, an annular member 302 may be telescopically seated onto proximal end 284, with the tabs 300 received in the corresponding slot arrangements 286. A cannulation inside diameter 304 is again provided in means 290, particularly shown by the inside diameter of annular member 302.

As shown by FIGS. 13 and 15, the securement means 292 may comprise a locking nut 306, which also has a cannulation inside diameter 308. It is with such locking nut 306 that the control arm means 290 are removably secured to the intramedullary rod proximal end connection thread means 236. It will be understood by those of ordinary skill in the art that the extension member 242, in essence, forms part of such rod proximal structure to and with which mounting of the various further devices in accordance with the subject invention may be practiced. The threads along inside diameter 308 of locking nut 306 are in fact received about the threaded portion 246 of such extension member 242, as clearly represented in present FIGS. 13 and 15. Annular member 302 of control arm means 290 in fact is received about the relatively smooth outside diameter portion 310 of such extension member 242.

Still further, the interlocking screw guide means 280 may include selectively operable clamping means generally 294, which are movably supported (preferably slidably) on the lateral extension or extension arm 298 of control arm means 290. See FIGS. 13 and 15. FIG. 14 is in fact an enlarged cross-sectional view of specific clamping means features in accordance with the exemplary embodiment of present FIG. 13, taken along the sectional line 14—14 indicated therein. With such an arrangement, the clamping means 294 may be selectively clamped on lateral arm 298 at a selected distance radially outward from the central longitudinal axis 312 of the intramedullary rod. Operatively, the purpose of such arrangement is to permit the position of targeting arm means generally 296 to be moved so as to match the size of a patient's leg into which the intramedullary rod is associated with the receiving femur.

Still further, such targeting arm means generally 296 may be variously secured to the clamping means 294 for movement therewith and extending therebelow for parallel alignment thereby with the central longitudinal axis 312 of the intramedullary rod. Such targeting arm means has at least one relatively proximal interlocking screw target hole 314 located a predetermined distance distal to clamping means 294. Such target hole 314 becomes aligned with the intramedullary rod relatively proximal interlocking screw hole 240 by virtue of the present arrangement, so that such hole 240 may be targeted for drilling through the femur and subsequently securing an interlocking screw in such hole 240. The same alignment approach permits additional target hole 316 to become aligned with corresponding additional interlocking screw hole 282 of the intramedullary rod.

More particularly, the control arm means lateral extension arm 298 has a predetermined cross-sectional shape (see FIG. 14) defined at least in part by at least one guide surface. The clamping means generally 294 includes one clamping surface to be selectively and correspondingly matched with such extension arm guide surface, and being movable relative to such matched guide surface so that the clamping means can be selectively engaged in a given position slidably along the extension arm (along the direction of double-headed arrow 318 of present FIG. 13). As stated, it is such arrangement which permits the overall targeting apparatus to be custom fitted to the leg size of a given patient.

The targeting arm means 296 may be integrally associated with the clamping means 294 (as represented by present FIG. 14), or may otherwise be attached thereto. Looking to all FIGS. 13 through 15, clamping means 294 may be provided in the form of a clamp plate housing generally 320 which is slidably and removably received about the lateral extension arm 298, and which may be integrally associated with the targeting arm means 296. Further, a clamp plate 322 may be provided movably residing between the lateral extension arm 298 and an inside surface 324 of clamp plate housing 320. A clamp plate bolt 326 with capture member 328 may be threadably received through the clamp plate housing 320 and positioned so as to selectively drive the clamp plate 322 into clamping engagement with the lateral extension arm 298.

By way of specific example, the lateral extension arm 298 is shown to have a cross-sectional shape utilizing six different guide surfaces comprising substantially a rectangle (in this example) with two bevelled edges 330 and 332 respectively connecting a first guide surface 334 of such rectangle to the two adjacent guide surfaces 336 and 338 thereof. A lower surface 340 completes the rectangle, all of which surfaces are surrounded and enclosed by clamp plate housing 320. While clamping surfaces may be provided for correspondingly matching with such six guide surfaces, not all such surfaces may actually need to be brought into engagement or contact in order for clamping to be effected. For example, as shown in present FIG. 14, the clamp plate housing 320 provides three internal surfaces (unreferenced) for contacting guide surfaces 336, 338, and 340, respectively. At the same time, the clamp plate provides surfaces (unreferenced) for respective contact with guide surfaces 330 and 332, though a gap is preferably maintained between guide surface 334 and the clamp plate in order to accommodate the end of clamp screw 326 and its securement ring or element 328. Those of ordinary skill in the art will appreciate that different embodiments of such clamping arrangements may be practiced in accordance with the subject invention, in keeping with the broader teachings herewith.

Those of ordinary skill in the art will appreciate that the interlocking screw guide means generally 280 discussed above, as well as the different embodiments of present exemplary driving means 252 and 254, may be removably associated with intramedullary rod embodiments in accordance with this invention. Such operative connection and subsequent removal thereof permits overall alternative accompanying devices to be utilized. For example, FIG. 16 illustrates a side elevational view, with partial cutaway, of a further example of a present rotational positional control arm generally 342, in accordance with the subject invention and providing a 90 degree drive feature.

More specifically, a threaded coupling 344 may be provided for mating with internal diameter threads 236 of a given intramedullary rod, while projecting tabs 346 and 348 may interface with registration slots 286 of the intramedullary rod. The purpose of such registration coupling is to ensure a fixed position of coupling element 350 so that torque may be applied to member 344 via 90 degree bevelled drive gear arrangement generally 352 and elongated drive coupling 354. In other words, as is well understood by those of ordinary skill in the art, drive power or rotational force applied to drive connection 356 will be translated into drive force about the longitudinal axis of coupling 344. A hex drive of 356 or similar may be utilized.

Again, a cannulation inside diameter 358 may be provided throughout the device for use with a nail insertion guide rod. In other words, cannulation inside diameter 358 extends throughout device 352 from the top side 360 thereof to the distal most portion 362 thereof.

In addition, a portion of the cannulation inside diameter 358 may include thread connections 363 for receiving a slide hammer driving means such as means 254, or a hammer block connection 252, preferably coupled through or with an element such as extension member 242. With the foregoing arrangement, rotational alignment of the intramedullary rod may be practiced with mechanical advantage, during the driving phase. Those of ordinary skill in the art will appreciate that such device 342 may be utilized and then removed from the intramedullary rod, so as to permit additional or alternative devices to be applied thereto.

FIG. 17 represents still further alternative devices in accordance with the subject invention, illustrating an isometric exploded view of an alternative embodiment of a laterally extending clamp plate support generally 364 for use in place of means 290 of FIGS. 13 and 15. With such device, a different extension member 366 is provided with only one set of proximal screw threads 368 and distal threads 370, which may couple with threads (not shown) within the intramedullary rod proximal end 284 thereof. Other connection means may be practiced in given embodiments. Hence, as representatively shown in FIG. 17, the proximal end inside diameter 372 of the intramedullary rod may be alternatively made smooth bored rather than threaded.

The annular member generally 374 may include projecting tabs 376 and 378 for registration and coupling with slots 286, in the fashion as discussed above in conjunction with other embodiments of the subject invention. Similarly, a locking nut 380 may be provided for securing device 364 to the intramedullary rod, and cannulation inside diameters 382 may be provided throughout the arrangement, as before with other devices.

In addition, a further threaded connection 384 may be provided for receipt of driving means generally 386 direct therewith, and at an angle offset from the central axis 386 of the intramedullary rod. Lateral extension arm 388 may again be utilized with a clamping means 294 (not shown) in the same fashion as described above with reference to present FIGS. 13 through 15.

The arrangement of present FIGS. 13 through 15 may be utilized with still further alternative features in accordance with the subject invention. For example, FIG. 18 illustrates an isometric view of a further exemplary embodiment in accordance with this invention, illustrating features alternative to some of those of present FIG. 13, and particularly representing a neck or hip screw placement guide arm generally 390 for use with intramedullary rods in accordance with the subject invention.

The intramedullary rod arrangement of FIG. 13 is substantially reiterated in FIG. 18, and represents that an imaginary plane 392 may be shown in relation to relatively thin proximal segment 232 of the intramedullary rod. Such imaginary plane 392 represents the dividing plane between such relatively thin proximal segment 232 and the complementary femoral hip screw passageway provided thereby. While certain features discussed above may be utilized for targeting interlocking screw holes 240 and 282, the features of present FIG. 18 may be utilized for targeting or guiding femoral hip screws into the passageway formed therefor with the subject invention.

More particularly, the femoral hip screw placement guide means 390 in accordance with the subject invention may include an arm 394 which is integrally formed with or operatively associated with clamping means 294, similar to the fashion in which depending arm 296 was so associated. However, rather than providing target holes 314 and 316 as in FIGS. 13 and 15, arm 394 has a relatively reduced size (i.e., width) and is specifically positioned relative clamping means 294 so as to provide a guide surface 396 which is coplanar to imaginary plane 392.

Therefore, a treating physician utilizing the arrangement of FIG. 18, may utilize clamp bolt 326 for sliding clamping means 294 inwardly along arrow 318 towards the central axis 312 of the intramedullary rod, until the surface 398 of guide arm 394 is brought into contact with or proximity with the outside of a patient's leg. Thereafter, the treating physician may drill along and adjacent to the side 396 of arm 394, thereby drilling on the passageway-side of imaginary plane 392 so as to seat femoral hip screws in the passageway defined therefor by relatively thin proximal segment 232.

It will be further understood by those of ordinary skill in the art that, if desired, various indicia or markings may be applied to surface 400 of guide arm 394, so that axial depth along central axis 312 may be indicated in addition to indication of the imaginary plane 392. However, even without such indicia, the treating orthopedic physician will be very familiar with the axial position of the femur as to where the screws (such as exemplary screws 42, 44, and 46 of present FIGS. 1 through 3) are to be seated. It is only the planar guidance which would be otherwise missing without practice of the present FIG. 18 features and methodology in accordance with the subject invention.

Lastly, FIG. 19 illustrates an isometric exploded view of a proximal end over-reamer generally 402 which may be practiced during extraction or withdrawal of intramedullary rods in accordance with the present invention, and further illustrates elongated slide hammer removal features generally 404 which may also be practiced in accordance with the subject invention during extraction.

The extraction over-reamer means generally 402 of present FIG. 19 is provided for cutting bony growth from around the intramedullary rod reduced cross-sectional area 232 for removal of the intramedullary rod from a patient's healed femur. Such extraction over-reamer means generally 402 may comprise a generally cylindrical annular cutting member 406, shown in broken illustration in present FIG. 19. Such annular cutting member is sized to fit over the intramedullary rod proximal end 284 and to slide therealong over proximal shaft segment 230. Distally located saw teeth 408 are provided for cutting into the bones, while a proximally located drive coupling 410 permits rotational driving of the saw teeth. The hexdrive arrangement 410 may be power driven or mechanically coupled to a manual arrangement.

In terms of withdrawal methodology in accordance with the subject invention, once any sort of interlocking screws or femoral hip screws are removed, the extraction over-reamer means generally 402 may be utilized to cut the proximal shaft segment 230 free from any bony growth around relatively proximal segment 232. Thereafter, rod removal means generally 412 may be utilized, such as including a slide hammer device 404 and hook 414 and eye 416 connection operatively associated with a threadable member 418 for direct attachment via threads 420 and 236 to the intramedullary rod proximal end 284. Of course, different connection means 234 for such rod may be practiced, and connection element 418 would be modified accordingly. A hex coupling 422 may be provided to facilitate driving connection of member 418, as will be well understood by those or ordinary skill in the art.

Once member 418 is seated, hook 414 may be secured thereto, and slide hammer element 424 may be axially moved along the direction of double-headed arrow 426 for axial extraction of the intramedullary rod. As will be understood by those of ordinary skill in the art, a handle device generally 426 may be provided as well as a fixed element 428 against which slide hammer 424 may strike. A shaft 430 is provided for movement of such slide hammer element 424, and may be threadably coupled via threads 432 and 434 to the hook connection member 414. It will be further understood by those of ordinary skill in the art that alternatives may be practiced. For example, the hook portion 414 may be associated with the member 418, and the eye portion 416 associated with the threadable coupling 434.

Those of ordinary skill in the art will further understand and appreciate from the totality of the foregoing disclosure, that the various alternative features and components shown and discussed in conjunction with FIGS. 12 through 19, may be practiced in accordance with various installation and withdrawal metholodologies, all of which combinations are intended to come within the spirit and the scope of the present, without rediscussion thereof. Such alternative methodologies are intended to include the use of different intramedullary rod embodiments practiced in accordance with the invention.

In addition to the foregoing, different embodiments such as including different numbers and placements of interlocking screws, or use of different femoral hip screws and neck screws, may be practiced. Likewise, it is to be fully understood by those of ordinary skill in the art that the foregoing structures and methodologies may be practiced for the treatment of various types and degrees of combination shaft and hip (or neck) ipsilateral fractures, without further detailed discussion of such different fracture types and degrees, as alluded to above in the Background and Summary portions of the subject specification.

It should be further understood by those of ordinary skill in the art that the foregoing presently preferred embodiments are exemplary only, and that the attendant description thereof is likewise by way of words of example rather than words of limitation, and their use does not preclude inclusion of such modifications, variations, and/or additions to the present invention (either apparatus or methodology) as would be readily apparent to one of ordinary skill in the art, the scope of the present invention being set forth in the appended claims.

What is claimed is:

1. A femoral intramedullary rod for the biomechanically stable anatomic reduction of a femoral shaft fracture while facilitating the independent treatment of an ipsilateral femoral hip fracture, said intramedullary rod comprising:

an elongated cannulated shaft with a tip end for being seated in a femoral shaft with said tip end introduced in a relatively distal direction through the proximal extremity of a receiving fractured femur; and a proximal cannulated substantially circular shaft segment associated in axial alignment with said elongated shaft, proximal to said elongated shaft and opposite to said shaft tip end, for residing generally in a femoral hip region whenever said elongated shaft is situated in a receiving femoral shaft, said proximal shaft segment including connection means for selectively interconnecting with drive components and extraction components for alternate installation and withdrawal, respectively, of the femoral intramedullary rod relative to a receiving femur, and said proximal shaft segment further including an elongated region of relatively reduced cross-sectional area spaced from and independent of said connection means defining a longitudinally elongated femoral hip screw passageway, said reduced cross-sectional area occupies an angular portion of an intermediate portion of said proximal shaft segment, said angular portion being only in a range of generally 180 degrees to 120 degrees of the circumference of said proximal shaft segment, said passageway thereby including to the longitudinal centerline of said proximal shaft segment so that femoral hip screws may be introduced through said passageway independently of and variably positionable relative said rod shaft into a femoral hip region through an angular range defined by said elongated femoral hip screw passageway for the treatment of fractures therein, and wherein said elongated region of relatively reduced cross-sectional area occupies one of a posterior and anterior portion.

2. A femoral intramedullary rod as in claim 1, wherein said cross-sectional area is generally constant throughout said elongated reduced cross-sectional area region.

3. A femoral intramedullary rod as in claim 2, wherein said cross-section area occupies an angular portion of an annular region, the outside diameter of which annular region is generally coaxial with the outside diameter of said proximal shaft segment.

4. A femoral intramedullary rod as in claim 3, wherein said angular portion occupies generally about 180 degrees of said annular region, and said connection means comprises internal diameter threads formed in said proximal cannulated shaft segment on the proximal side of said elongated region of relatively reduced cross-sectional area thereof, so that axial rod installation forces may be transmitted through said elongated region of relatively reduced cross-sectional area.

5. A femoral intramedullary rod as in claim 3, wherein said connection means includes internal diameter threads formed in said proximal cannulated shaft segment on the distal side of said relatively reduced cross-sectional area region thereof, so that axial rod installation forces are not transmitted through said elongated reduced cross-sectional area region.

6. A femoral intramedullary rod as in claim 3, wherein said connection means comprises a plurality of threads formed on at least a portion of the inside diameter of said proximal cannulated shaft segment.

7. A femoral intramedullary rod as in claim 6, wherein said threads are formed only proximally relative to said elongated reduced cross-sectional area region.

8. A femoral intramedullary rod as in claim 6, wherein said threads are formed both proximally and distally relative to said elongated reduced cross-sectional area region.

9. A femoral intramedullary rod as in claim 1, wherein said elongated shaft, between said tip end thereof and said proximal shaft segment axially associated therewith, has a radius of curvature generally in a range of from about one meter to about three meters, so as to match the natural curvature of a patient's femur.

10. A femoral intramedullary rod as in claim 9, wherein said tip end of said elongated shaft is generally tapered, and further wherein said elongated shaft, between said tapered tip end thereof and said proximal shaft segment axially associated therewith, has an outside diameter which falls generally in a range of from about 10 millimeters to about 16 millimeters.

11. A femoral intramedullary rod as in claim 10, wherein said intramedullary rod includes at least one interlocking screw hole at a predetermined axial distance from the proximal end of said rod, and said rod further includes registration means associated with said proximal end for subsequent targeting of said interlocking screw hole.

12. A femoral intramedullary rod as in claim 11, wherein said intramedullary rod includes at least one interlocking screw hole in a relatively proximal location in said rod shaft, and at least one interlocking screw hole in a relatively distal location in said rod shaft, and wherein said registration means comprises at least one registration slot formed in said rod proximal end, said registration slot having a predetermined rotational relationship with said interlocking screw holes so as to serve as a guide to the locations thereof.

13. A femoral intramedullary rod as in claim 11, wherein said intramedullary rod has a total length generally in a range of from about 300 millimeters to about 500 millimeters.

14. A femoral intramedullary rod as in claim 13, wherein the outside diameter of said proximal shaft segment is greater than said outside diameter of said elongated shaft.

15. A femoral intramedullary rod as in claim 11, wherein said outside diameter of said elongated shaft, between said tapered tip end thereof and said proximal shaft segment axially associated therewith, has a substantially constant cross-sectional shape of one of cylindrical, slotted and fluted.

16. A femoral intramedullary rod as in claim 1, further including:
a complementary modular element for attachment to said proximal shaft segment and configured so as to fill in said femoral hip screw passageway thereof; and
modular element attachment means for selectively attaching said modular element to said proximal shaft segment.

17. A femoral intramedullary rod as in claim 16, wherein:
said elongated femoral hip screw passageway comprises at least one-half of the cross-section of said elongated reduced cross-sectional area region;
said modular element has an exterior shape of an elongated semicircle so as to matably fill said femoral hip screw passageway; and
said modular element attachment means comprises aligned attachment screw holes formed respectively in said modular element and said proximal shaft segment, and attachment screws for securing said modular element to said proximal shaft segment.

18. A femoral intramedullary rod as in claim 1, wherein said proximal shaft segment is integrally formed with said elongated shaft.

19. A femoral intramedullary rod as in claim 1, wherein:
said proximal shaft segment and said elongated shaft comprise respective, axially matable members; and said intramedullary rod further includes joining means for axially joining said respective proximal shaft segment and said elongated shaft in mated axial arrangement.

20. A femoral intramedullary rod as in claim 19, wherein said proximal shaft segment has a predetermined selected shape for said elongated reduced cross-sectional area region thereof, so as to provide a treating physician with a selected location for said elongated femoral hip screw passageway customized for the femoral hip fracture treatment of a given patient.

21. A femoral intramedullary rod as in claim 20, wherein:
said proximal shaft segment and said elongated shaft are telescopically related to one another; and
said joining means comprise aligned screw holes on the respective proximal shaft segment and elongated shaft, and connecting bolts receivable therein.

22. A femoral intramedullary rod as in claim 1, wherein:
said proximal shaft segment includes an increased cross-sectional area;
said elongated reduced cross-sectional area occupies a generally posterior position, covering in a range of from about ⅓ to about ½ of said increased proximal shaft segment cross-sectional area;
said elongated shaft between said tip end thereof and said proximal shaft segment has a radius of curvature generally in a range of from about 1.0 to 1.75 meters, and has a generally cylindrical cross-section;
said connection means comprises threads formed in the inside diameter of said proximal cannulated shaft segment; and
said intramedullary rod further includes a plurality of interlocking screw holes formed therein at respective predetermined distal distances from the proximal end of said intramedullary rod, and said intramedullary rod further includes registration means at said rod proximal end for subsequent targeting of said interlocking screw holes.

23. A femoral intramedullary rod as in claim 1, wherein:
said elongated reduced cross-sectional area occupies a generally anterior position, covering in a range of from about ⅓ to about ½ of the cross-sectional area of said proximal shaft segmented;
said elongated shaft between said tip end thereof and said proximal shaft segment has a radius of curvature generally in a range of from about 1.0 to 1.75 meters, and has a generally cylindrical cross-section;
said connection means comprises threads formed in the inside diameter of said proximal cannulated shaft segment; and
said intramedullary rod further includes a plurality of interlocking screw holes formed therein at respective predetermined distal distances from the proximal end of said intramedullary rod, and said intramedullary rod further includes registration means at said rod proximal end for subsequent targeting of said interlocking screw holes.

* * * * *